US007084303B2

(12) United States Patent
Watanabe et al.

(10) Patent No.: US 7,084,303 B2
(45) Date of Patent: Aug. 1, 2006

(54) TERTIARY AMINE COMPOUNDS HAVING AN ESTER STRUCTURE AND PROCESSES FOR PREPARING SAME

(75) Inventors: Takeru Watanabe, Niigata-ken (JP); Koji Hasegawa, Niigata-ken (JP); Takeshi Kinsho, Niigata-ken (JP); Jun Hatakeyama, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 405 days.

(21) Appl. No.: 10/127,120

(22) Filed: Apr. 22, 2002

(65) Prior Publication Data

US 2002/0193622 A1 Dec. 19, 2002

(30) Foreign Application Priority Data

Apr. 23, 2001 (JP) ............................. 2001-123927

(51) Int. Cl.
C07C 211/00 (2006.01)
(52) U.S. Cl. .................. 564/463; 564/462; 564/502
(58) Field of Classification Search ............... 562/512, 562/553, 567, 568, 571, 573, 575, 576; 560/253; 564/503
See application file for complete search history.

(56) References Cited

U.S. PATENT DOCUMENTS

| 2,729,622 | A | | 1/1956 | Albisetti et al. |
| 4,115,232 | A | * | 9/1978 | Nyi et al. ................ 522/14 |
| 4,491,628 | A | | 1/1985 | Ito et al. |
| 5,023,283 | A | * | 6/1991 | Ravichandran et al. ..... 524/239 |
| 5,580,695 | A | | 12/1996 | Murata et al. |
| 5,609,989 | A | | 3/1997 | Bantu et al. |
| 5,968,712 | A | | 10/1999 | Thackeray et al. |
| 6,673,511 | B1 | * | 1/2004 | Hatakeyama et al. .... 430/270.1 |
| 2001/0038964 | A1 | | 11/2001 | Thackery et al. |

FOREIGN PATENT DOCUMENTS

| EP | 0 412 457 | 2/1991 |
| EP | 0 537 524 | 4/1993 |
| EP | 0 558 280 | 9/1993 |
| EP | 0 249 139 B1 | 7/1994 |
| JP | 63-149640 A | 6/1988 |
| JP | 5-113666 A | 5/1993 |
| WO | WO 98/37458 A | 8/1998 |

OTHER PUBLICATIONS

Hughes et al., Synthesis and peripheral vasodilatator activity of alpha-(1-(4-piperidylamino)alkyl)benzyl alcohols, *Journal of Medicinal Chemistry*, vol. 14, No. 9, 1971, XP002249251 American Chemical Society, Washington, US ISSN: 0022-2623, p. 895.
Patent Abstracts of Japan, vol. 2000, No. 24, May 11, 2001 & JP 2001 194776 (Shin Etsu Chem Co Ltd) Jul. 19, 2001.
Hinsberg et al., "Fundamental Studies of Airborne Chemical Contamination of Chemically Amplified Resists," *Journal of Photopolymer Science and Technology*, vol. 6, No. 4, pp. 535-546 (1993).
Kumada et al., "Study on Over-Top Coating of Positive Chemical Amplification Resists for KrF Excimer Laser Lithography," *Journal of Photopolymer Science and Technology*, vol. 6, No. 4, pp. 571-574 (1993).
Hatakeyama et al., "Investigation of Discrimination Enhancement of Polysilsesquioxane Based Positive Resist for ArF Lithography," *SPIE*, vol. 3333, pp. 62-72 (1998).
Hatakeyame et al., "Investigation of Discrimination Enhancement with New Modeling for Poly-Hydroxystyrene Positive Resists," *Journal of Photopolymer Science and Technology*, vol. 13, No. 4, pp. 519-524 (2000).

* cited by examiner

*Primary Examiner*—Johann Richter
*Assistant Examiner*—Karl Puttlitz
(74) *Attorney, Agent, or Firm*—Alston & Bird LLP

(57) ABSTRACT

The present invention provides ester group-containing tertiary amine compounds of the formula $(R^1OCH_2CH_2)_nN(CH_2CH_2CO_2R^2)_{3-n}$ which, when used as additives in chemical amplification photolithography, can yield photoresists having a high resolution and an excellent focus margin. The present invention also provides a process comprising the step of subjecting a primary or secondary amine compound to Michael addition to an acrylic ester compound; a process comprising the steps of subjecting monoethanolamine or diethanolamine to Michael addition to an acrylic ester compound so as to form an ester group-containing amine compound and introducing a $R^1$ group to the resultant ester group-containing amine compound; and a process comprising the step of effecting the ester exchange reaction of an ester group-containing tertiary amine with $R^2OH$.

8 Claims, No Drawings

US 7,084,303 B2

TERTIARY AMINE COMPOUNDS HAVING AN ESTER STRUCTURE AND PROCESSES FOR PREPARING SAME

BACKGROUND OF THE INVENTION

1. Filed of the Invention

This invention relates to novel ester group-containing tertiary amine compounds which are useful as additives for novel chemical amplification resists suitable for fine processing techniques.

2. Description of the Related Art

While increasingly finer pattern rules are required as the degree of integration and speed of LSIs become higher, far ultraviolet lithography is regarded as a promising fine processing technique of the next generation. Far ultraviolet lithography is capable of processing down to a size of 0.2 µm or less, and when a resist material having low light absorption is used, permits the formation of patterns having sidewalls substantially perpendicular to the substrate. Moreover, a technique using a high luminance KrF excimer laser as the light source of far ultraviolet radiation is attracting attention in recent years. In order to employ this technique as a mass production technique, a resist material having low light absorption and high sensitivity is desired.

From this point of view, chemically amplified positive resist materials using an acid as the catalyst have recently been developed (as disclosed, for example, in Japanese Patent Publication No. 2-27660/'90 and Japanese Patent Provisional Publication No. 63-27829/'88). These resist materials have excellent characteristics such as high sensitivity, high resolution and high dry etching resistance, and are hence particular promising for use in far ultraviolet lithography.

One disadvantage of chemically amplified resists is that, if the resist is allowed to stand for a long time between light exposure and PEB (Post Exposure Bake), the formed line patters have a T-top shape, i.e. the patterns have a thickened upper part (this problem is referred to as PED (Post Exposure Delay)). Another disadvantage is the so-called footing phenomenon in which the lower part of the patterns is thickened in the neighborhood of the substrate especially when the substrate comprises a basic material such as silicon nitride or titanium nitride. It is considered that the T-top phenomenon is due to a reduction in the solubility of the resist film at the surface, and the footing phenomenon on the substrate surface is due to a reduction in the solubility of the resist film in the neighborhood of the substrate. Moreover, a problem arises in that a dark reaction eliminating an acid-labile group proceeds during a period of time extending from light exposure to PEB, resulting in a reduction in line dimensions.

These problems present serious drawbacks when chemically amplified resists are put to practical use. Owing to these drawbacks, conventional chemically amplified positive resist materials have been unsatisfactory in that dimensional control is difficult not only in lithographic steps but also in substrate processing by dry etching (see, for example, W. Hinsberg et al., J. Photopolym. Sci. Technol., 6(4), 535–546(1993); and T. Kumada et al., J. Photopolym. Sci. Technol., 6(4), 571–574(1993)).

In chemically amplified positive resist materials, the problems of PED and footing on the substrate surface are considered to be closely related to basic compounds present in air or on the substrate surface. The acid formed in the surface of the resist film by exposure to light is inactivated by reaction with basic compounds in air. As the standing time till PEB is prolonged, the amount of acid inactivated increases and, therefore, the acid-labile group becomes hard to decompose. Consequently, a hardly soluble layer is formed at the film surface and the patterns assume a T-top shape.

It is well known that the addition of a basic compound suppresses the influence of basic compounds in air and is hence effective against PED (U.S. Pat. No. 5,609,989, WO 98/37458, Japanese Patent Provisional Publication No. 63-149640/'88, Japanese Patent Provisional Publication No. 5-113666/93, Japanese Patent Provisional Publication No. 5-232706/'93 (U.S. Pat. No. 5,580,695) and Japanese Patent Provisional Publication No. 5-249662/'93 (U.S. Pat. No. 5,968,712 and 20010038964)).

Well-known basic compounds are nitrogen-containing compounds such as amine compounds and amide compounds having a boiling point of 150° C. or above. Specific examples thereof include polyvinylpyridine, aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and triazine compounds such as 2-(p-chlorophenyl)-4,6-trichloromethyl-s-triazine. Among them, pyrrolidone, N-methylpyrrolidone, o-aminobenzoic acid, m-aminobenzoic acid, p-aminobenzoic acid and 1,2-phenylenediamine are especially preferred.

These nitrogen-containing compounds are weak bases, and can mitigate the T-top problem. However, when a highly reactive acid-labile group (e.g., an acetal group such as 1-ethoxyethyl) is used, it is impossible to control the reaction, i.e., the diffusion of the acid. The addition of a weak base has been disadvantageous especially in that the dark reaction during PED proceeds in unexposed regions and causes a reduction in line size (slimming) and a film loss at the line surface in the case of an acetal-derived acid-labile leaving group. In order to solve these problems, it has been effective to add a strong base. However, it may not be definitely said that a compound having a higher basicity is more effective. In fact, the addition of so-called superstrong bases such as DBU (1,8-diazabicyclo[5.4.0]-7-undecene), DBN (1,5-diazabicyclo[4.3.0]-5-nonene), proton sponge, and quaternary amines (e.g., tetramethylammonium hydroxide) has failed to produce a sufficient effect.

The effects produced by the addition of a basic compound to a resist composition include not only an improvement in environmental stability, but also an enhancement in resolution. The addition of a base reduces sensitivity, but enhances contrast in acid release. In exposed regions where the number of moles of the acid released is smaller than the number of moles of the base added, the acid is inactivated by neutralization with the base, and is unable to cause a catalytic reaction. However, as soon as the neutralization point is exceeded, an acid is suddenly released to cause a catalytic reaction.

The phenomenon of sudden acid release induced by the addition of a base in the vicinity of the neutralization point was called a proton jump by Hatakeyama et al. (SPIE Symp. Proc., 3333, 62(1998)). Moreover, Hatakeyama et al. carried out a close investigation on the mechanism of a proton jump and proposed a competitive reaction theory that the neutralization reaction between the acid formed by exposure to light and the base takes place at the same time as the reaction catalyzed by the acid occurs (J. Photopolymer. Sci. Technol., Vol. 13(4), p. 519(2000)). They solved kinetically the neutralization reaction between the acid formed photochemically and the base added, and showed that a base having a greater reaction rate constant can give higher contrast.

SUMMARY OF THE INVENTION

Our experiments performed by the addition of various bases have revealed that there is no close relationship between the reaction rate constant and pKa of acids. For example, triethanolamine having a lower basicity has been found to have a greater reaction rate constant than so-called superstrong bases such as DBU (1,8-diazabicyclo[5.4.0]-7-undecene), DBN (1,5-diazabicyclo[4.3.0]-5-nonene), proton sponge, quaternary amines (e.g., tetramethylammonium hydroxide), sodium hydroxide and potassium hydroxide. Moreover, tris[2-(methoxymethoxy)-ethyl]amine and tris[2-{(2-methoxyethoxy)methoxy}ethyl]amine have been found to have a greater reaction rate constant and give higher contrast than triethanolamine. In this connection, these bases are estimated to have a pKa of around 7, and are much weaker bases than DBU, DBN, quaternary ammonium hydroxide and proton sponge that have a pKa of the order of 13.

From these facts, it has been made clear that the bases added to resists need not be superstrong bases, but amines having a polar functional group such as a hydroxyl or ether group are effective. However, even these bases are not satisfactorily effective in preventing a film loss, enhancing the contrast, and extending the focus margin. Accordingly, there is a need for the development of a more suitable base.

The present invention has been made in view of the above-described circumstances, and an object thereof is to provide novel and useful ester group-containing tertiary amine compounds which, when used as additives in chemical amplification photolithography, can yield photoresists having a high resolution and an excellent focus margin, as well as processes for preparing these compounds.

The present inventors carried out intensive investigations with a view to accomplishing the above object. As a result, it has been found that tertiary amines having a specific structure containing an ester group as represented by the following general formula (1) can be obtained in high yields and with simplicity by employing any of the processes which will be described later, and that these ester group-containing tertiary amine compounds are highly effective in preventing a loss of the resist film, enhancing the resolution, and extending the focus margin.

That is, the present invention provides ester group-containing tertiary amine compounds represented by the following general formula (1). Moreover, as processes for the preparation of ester group-containing tertiary amine compounds represented by the following general formula (1), the present invention also provides a process comprising the step of subjecting a primary or secondary amine compound represented by the following general formula (5) to Michael addition to an acrylic ester compound represented by the following general formula (6); a process comprising the steps of subjecting monoethanolamine or diethanolamine represented by the following general formula (7) to Michael addition to an acrylic ester compound represented by the following general formula (6) so as to form an ester group-containing amine compound represented by the following general formula (8), and introducing the following $R^1$ group thereinto; and a process comprising the step of effecting the ester exchange reaction of an ester group-containing tertiary amine represented by the following general formula (9), with $R^2OH$.

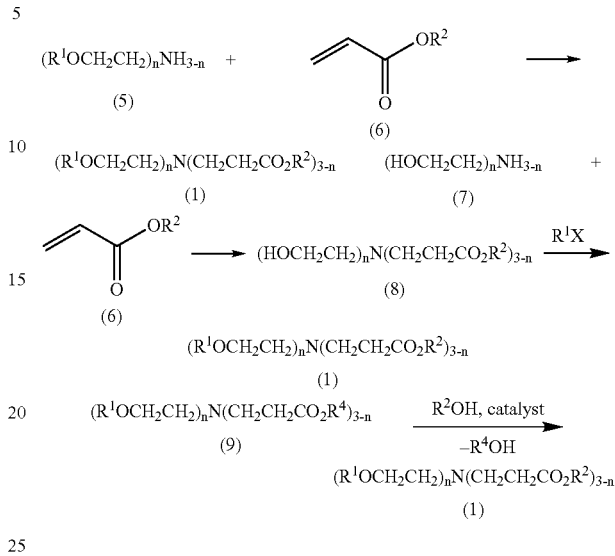

wherein n is 1 or 2; $R^1$ and $R^2$ each independently represent a straight-chain, branched or cyclic alkyl group of 1 to 20 carbon atoms which may contain an ether, carbonyl or carbonyloxy group; $R^4$ represents an alkyl group of 1 to 4 carbon atoms; and X represents a leaving group such as halogen, alkylsulfonyloxy, acyloxy, hydroxyl or aryloxy.

Resist materials prepared by adding ester group-containing tertiary amine compounds in accordance with the present invention have a high resolution and an excellent focus margin, and are useful for fine processing with electron rays or far ultraviolet radiation. In particular, since their addition can produce an excellent effect in KrF resists, ArF resists, $F_2$ resists and EB resists, these resists are suitable for use as fine pattern forming materials for the manufacture of VLSIs.

DETAILED DESCRIPTION OF THE PREFERRED EMBODIMENTS

The present invention will be more specifically described hereinbelow.

In the general formula (1) of the present invention, $R^1$ preferably has 1 to 10 carbon atoms and $R^2$ preferably has 2 to 10 carbon atoms. Such ester group-containing tertiary amine compounds can be represented by the following general formula (2).

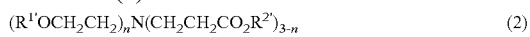

wherein n is 1 or 2; $R^{1'}$ each independently represents an alkyl group of 1 to 10 carbon atoms which may contain an ether, carbonyl or carbonyloxy group; and $R^{2'}$ represents a straight-chain, branched or cyclic alkyl group of 2 to 10 carbon atoms which may contain an ether, carbonyl or carbonyloxy group.

Moreover, in the general formula (1) of the present invention, $R^1$ is preferably a formyl or acetyl group and $R^2$ preferably has 2 to 10 carbon atoms. Such ester group-containing tertiary amine compounds can be represented by the following general formula (3).

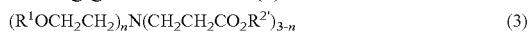

wherein n is 1 or 2; $R^{2'}$ represents a straight-chain, branched or cyclic alkyl group of 2 to 10 carbon atoms which may contain an ether, carbonyl or carbonyloxy group; and $R^1$ represents a formyl or acetyl group.

Furthermore, in the general formula (1) of the present invention, $R^1$ is preferably a methyl group and $R^2$ preferably has 2 to 10 carbon atoms. Such ester group-containing tertiary amine compounds can be represented by the following general formula (4).

$$(CH_3OCH_2CH_2)_nN(CH_2CH_2CO_2R^{2'})_{3-n} \quad (4)$$

wherein n is 1 or 2; and $R^{2'}$ represents a straight-chain, branched or cyclic alkyl group of 2 to 10 carbon atoms which may contain an ether, carbonyl or carbonyloxy group.

In the ester group-containing tertiary amine compounds of the general formulas (1) to (4) in accordance with the present invention, examples of $R^1$ include, but are not limited to, methyl, ethyl, propyl, isopropyl, butyl, s-butyl, isobutyl, t-butyl, pentyl, cyclopentyl, hexyl, cyclohexyl, decyl, methoxymethyl, 2-methoxyethyl, 1-ethoxyethyl, 2-ethoxyethyl, (2-methoxyethoxy)methyl, 2-tetrahydrofuranyl, 2-tetrahydropyranyl, tetrahydrofurfuryl, formyl, acetyl, propionyl, butyryl, isobutyryl, pivaloyl, valeryl, methoxyacetyl, ethoxyacetyl, acetoxyacetyl, 2-formyloxyethyl, 2-acetoxyethyl, 2-oxopropyl, 2-oxobutyl, 2-oxocyclopentyl, 2-oxo-3-tetrahydrofuranyl, 2-oxo-3-tetrahydropyranyl, methoxycarbonyl, ethoxycarbonyl and t-butoxycarbonyl.

In the ester group-containing tertiary amine compounds of the general formulas (1) to (4) in accordance with the present invention, examples of $R^2$ include, but are not limited to, methyl, ethyl, propyl, isopropyl, butyl, s-butyl, isobutyl, pentyl, isopentyl, cyclopentyl, hexyl, cyclohexyl, octyl, 2-ethylhexyl, decyl, stearyl, 2-methoxyethyl, 2-ethoxyethyl, 2-propoxyethyl, 2-isopropoxyethyl, 2-butoxyethyl, 2-cyclohexyloxyethyl, 2-methoxy-1-methylethyl, 3-ethoxypropyl, 3-butoxypropyl, 2-(2-methoxyethoxy)ethyl, 2-(2-ethoxyethoxy)ethyl, 2-[2-(2-methoxyethoxy)ethoxy]ethyl, 2-[2-(2-ethoxyethoxy)ethoxy]ethyl, 3-tetrahydrofuranyl, tetrahydrofurfuryl, 3-tetrahydrofuranylmethyl, 2-tetrahydropyranylmethyl, tetrahydro-4H-pyran-4-yl, 1,3-dioxan-5-yl, 1,3-dioxolan-4-ylmethyl, 2,2-dimethyl-1,3-dioxolan-4-ylmethyl, 2-formyloxyethyl, 2-acetoxyethyl, 2-propionyloxyethyl, 2-(methoxyacetoxy)ethyl, 2-(acetoxyacetoxy)ethyl, 2-(methoxycarbonyloxy)ethyl, 2-(ethoxycarbonyloxy)ethyl, 2-(butoxycarbonyloxy)ethyl, 2-(isobutoxycarbonyloxy)ethyl, 2-(t-butoxycarbonyloxy)ethyl, 2-(pentyloxycarbonyloxy)ethyl, 2-(hexyloxycarbonyloxy)ethyl, 2-(heptyloxycarbonyloxy)ethyl, 2-(octyloxycarbonyloxy)ethyl, 2-(2-nonyloxycarbonyloxy)ethyl, 2-(decyloxycarbonyloxy)ethyl, 2-(2-methoxyethoxycarbonyloxy)ethyl, 2-(methoxycarbonylmethoxy)ethyl, 2-(ethoxycarbonylmethoxy)ethyl, 4-formyloxybutyl, 4-acetoxybutyl, 4-propionyloxybutyl, 4-(methoxyacetoxy)butyl, 4-(acetoxyacetoxy)butyl, 4-(methoxycarbonyloxy)butyl, 2-(ethoxycarbonyloxy)butyl, 4-(butoxycarbonyloxy)butyl, 4-(isobutoxycarbonyloxy)butyl, 4-(t-butoxycarbonyloxy)butyl, 4-(pentyloxycarbonyloxy)butyl, 4-(hexyloxycarbonyloxy)butyl, 4-(heptyloxycarbonyloxy)butyl, 4-(octyloxycarbonyloxy)butyl, 4-(2-nonyloxycarbonyloxy)butyl, 4-(decyloxycarbonyloxy)butyl, 4-(2-methoxyethoxycarbonyloxy)butyl, formyloxypropyl, acetoxypropyl, 2-oxo-1-propyl, 2-oxo-1-butyl, 2-oxocyclopentyl, 2-oxocyclohexyl, 2-oxo-3-tetrahydrofuranyl and 2-oxo-3-tetrahydropyranyl.

Specific examples of the ester group-containing tertiary amine compounds of the present invention include, but are not limited to, the following compounds.

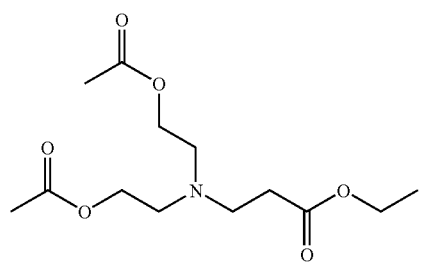

Amine 1

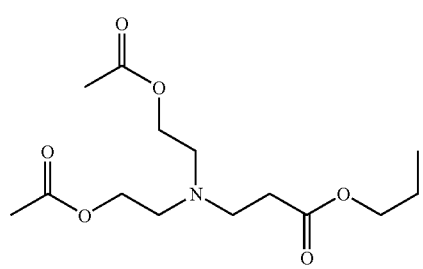

Amine 2

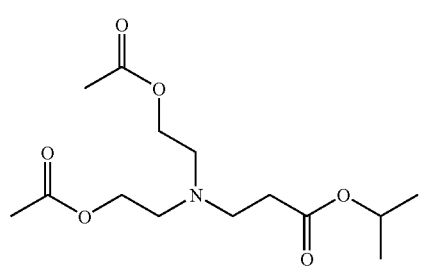

Amine 3

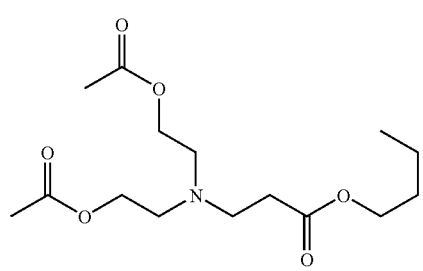

Amine 4

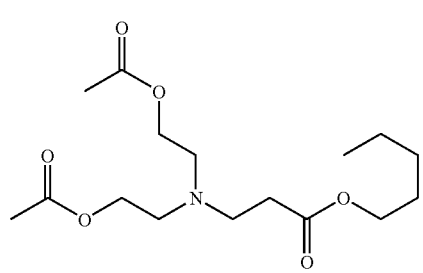

Amine 5

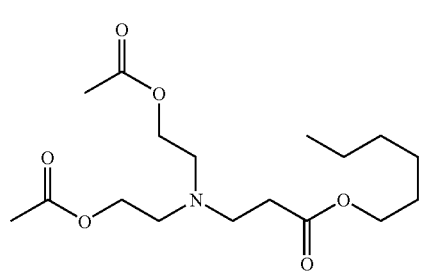

Amine 6

Amine 7
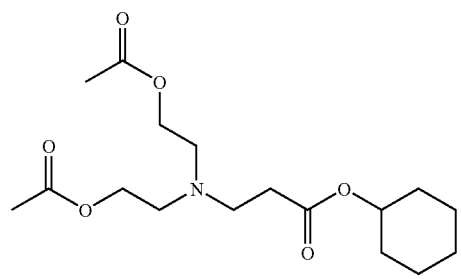
Amine 8
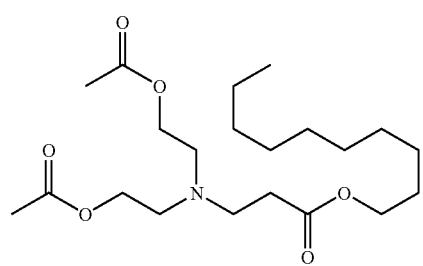
Amine 9
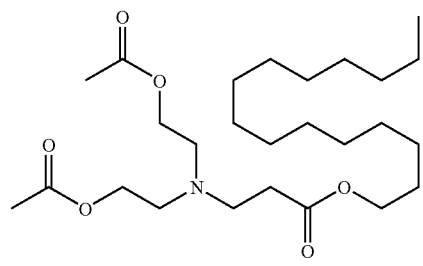
Amine 10
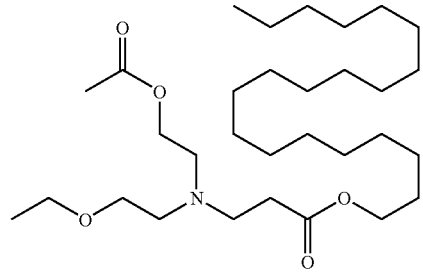
Amine 11
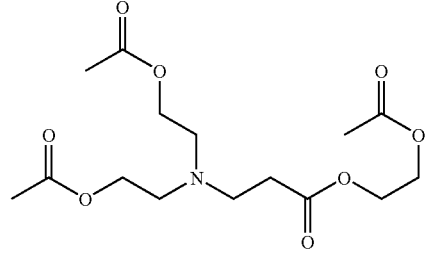
Amine 12
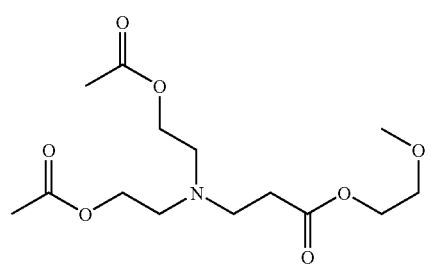
Amine 13
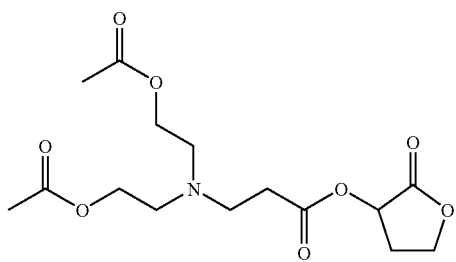
Amine 14
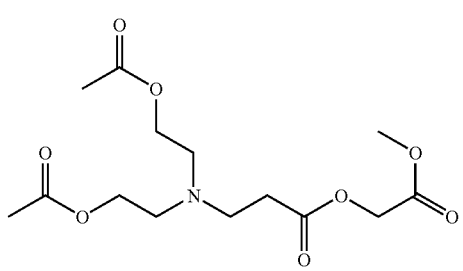
Amine 15
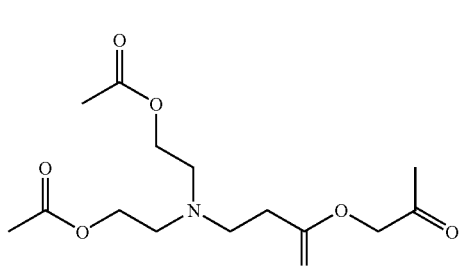
Amine 16
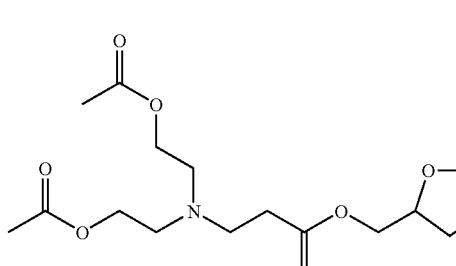
Amine 17
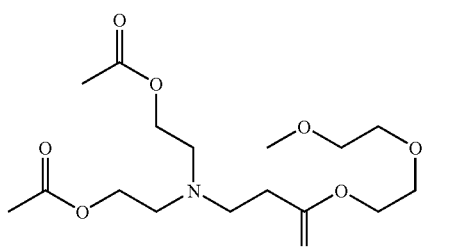
Amine 18
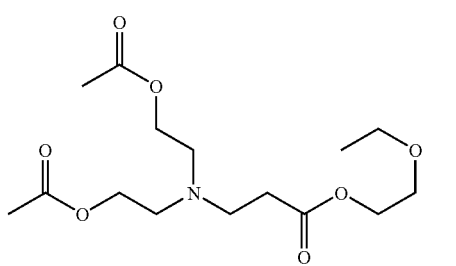

-continued
Amine 19
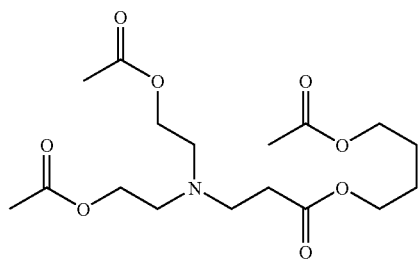
Amine 20
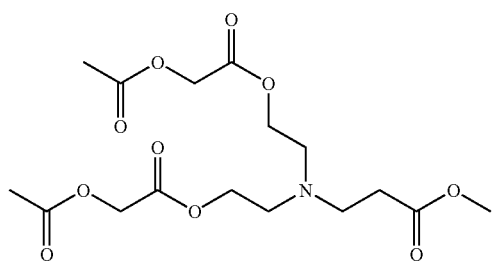
Amine 21
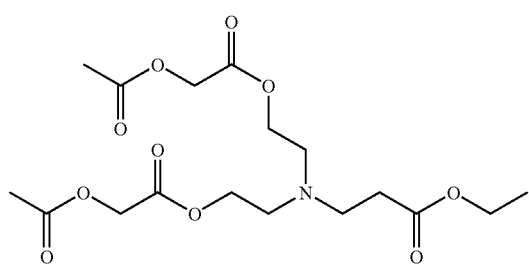
Amine 22
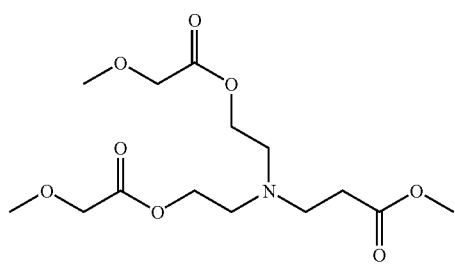
Amine 23
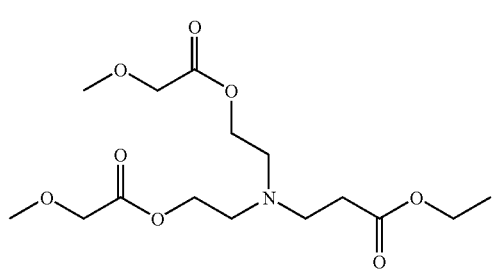
-continued
Amine 24
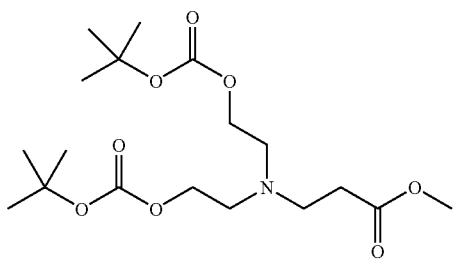
Amine 25
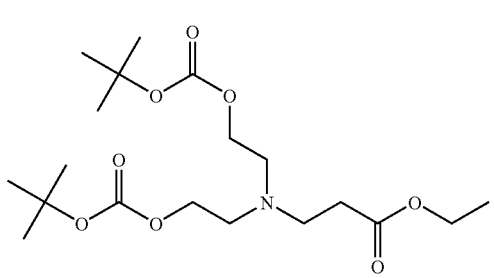
Amine 26
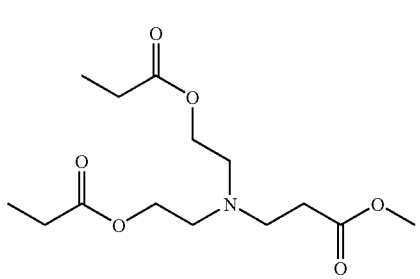
Amine 27
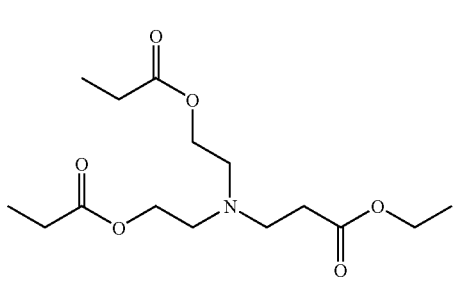
Amine 28
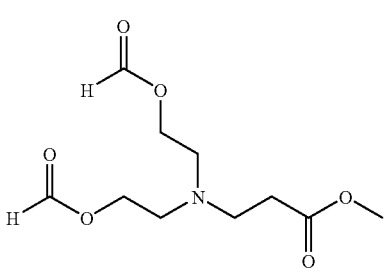

Amine 29
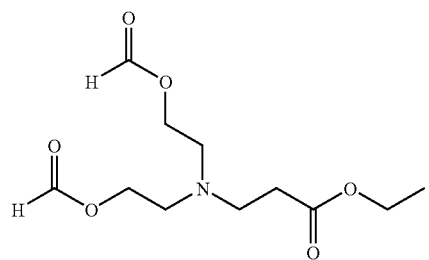
Amine 30
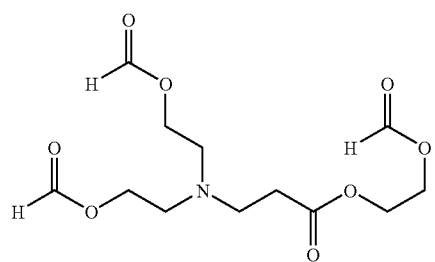
Amine 31
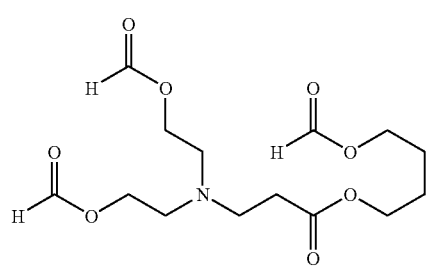
Amine 32
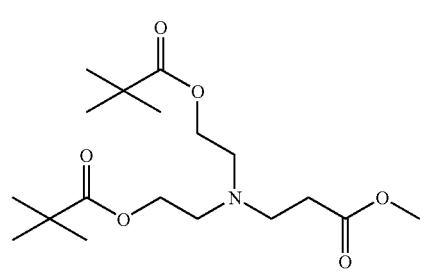
Amine 33
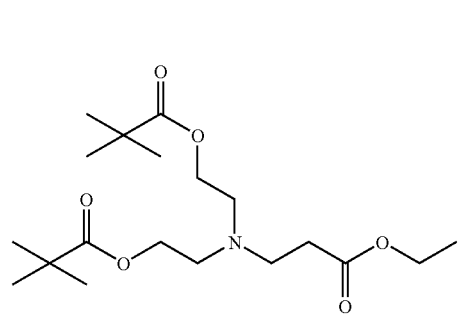
Amine 34
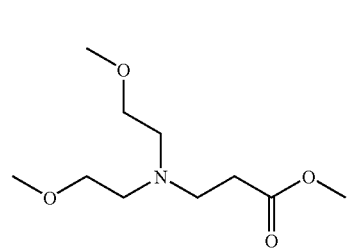
Amine 35
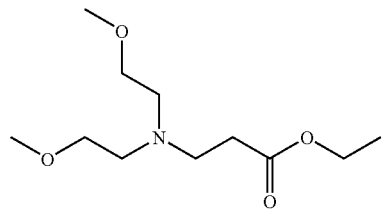
Amine 36
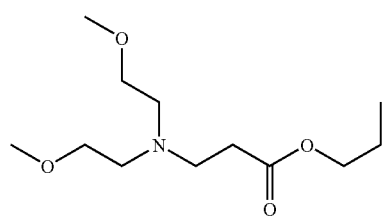
Amine 37
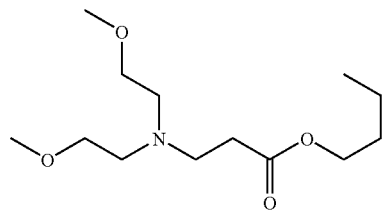
Amine 38
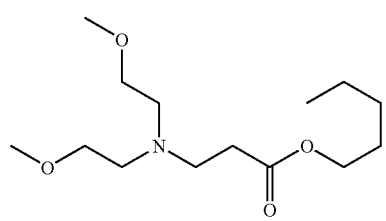
Amine 39
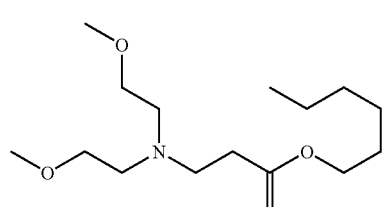
Amine 40
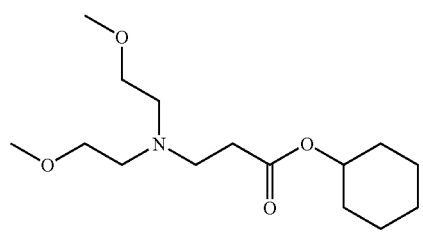
Amine 41

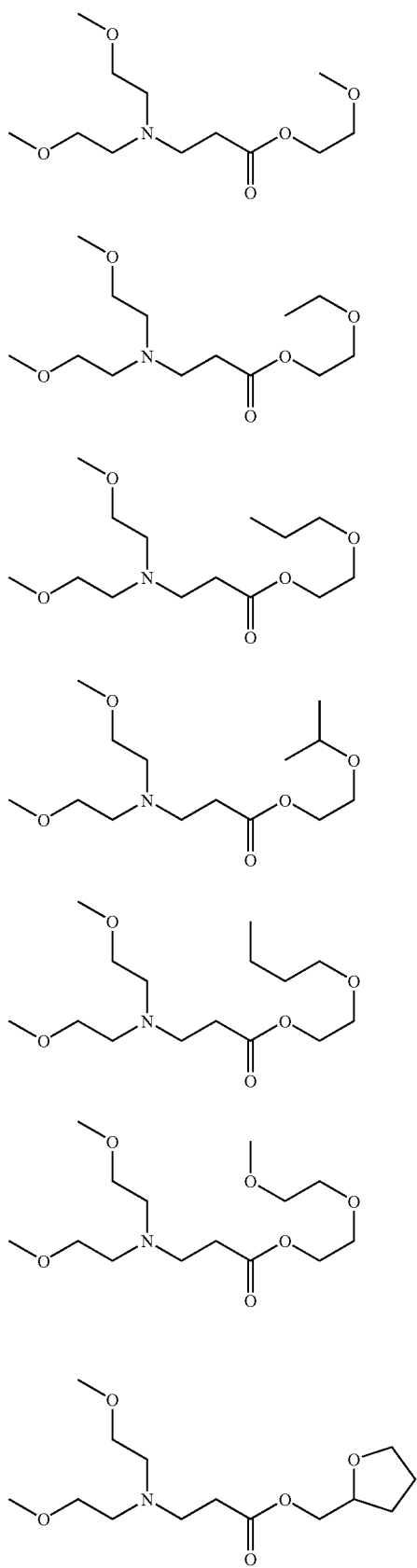
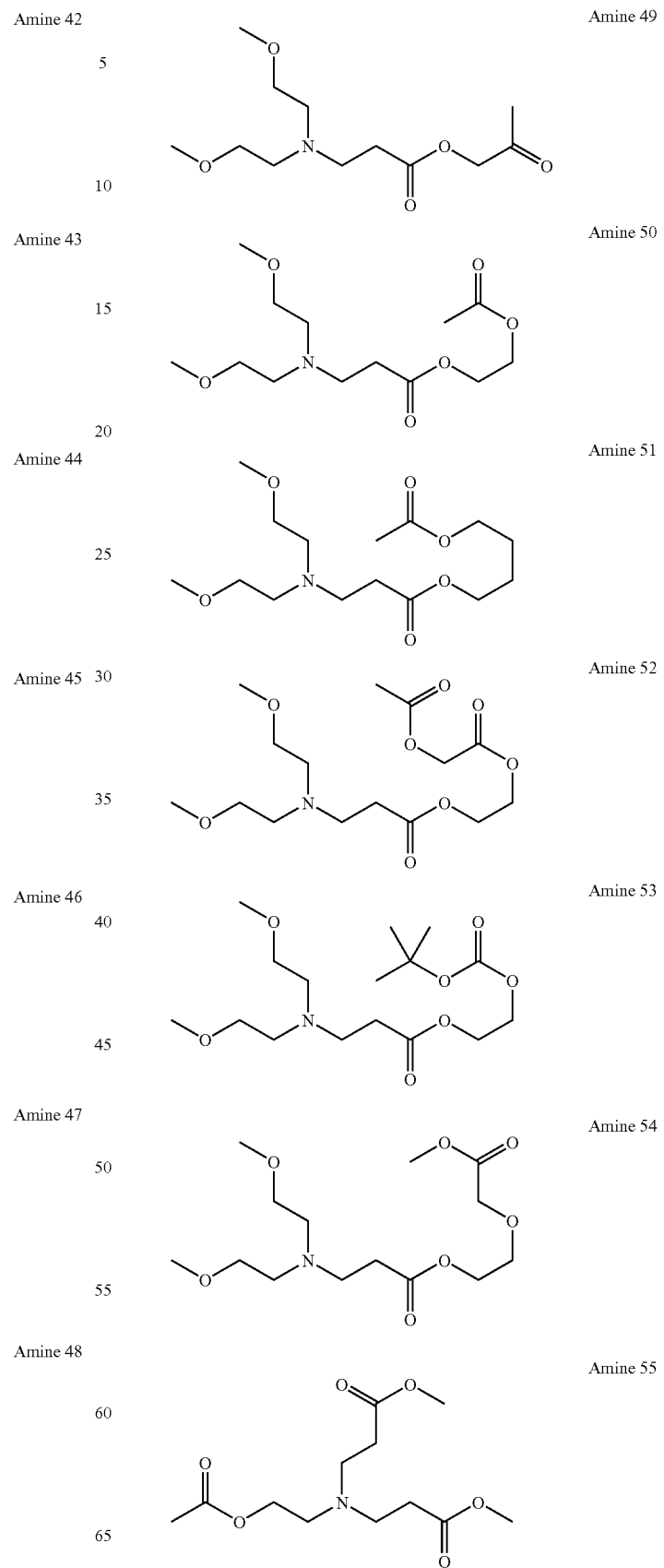

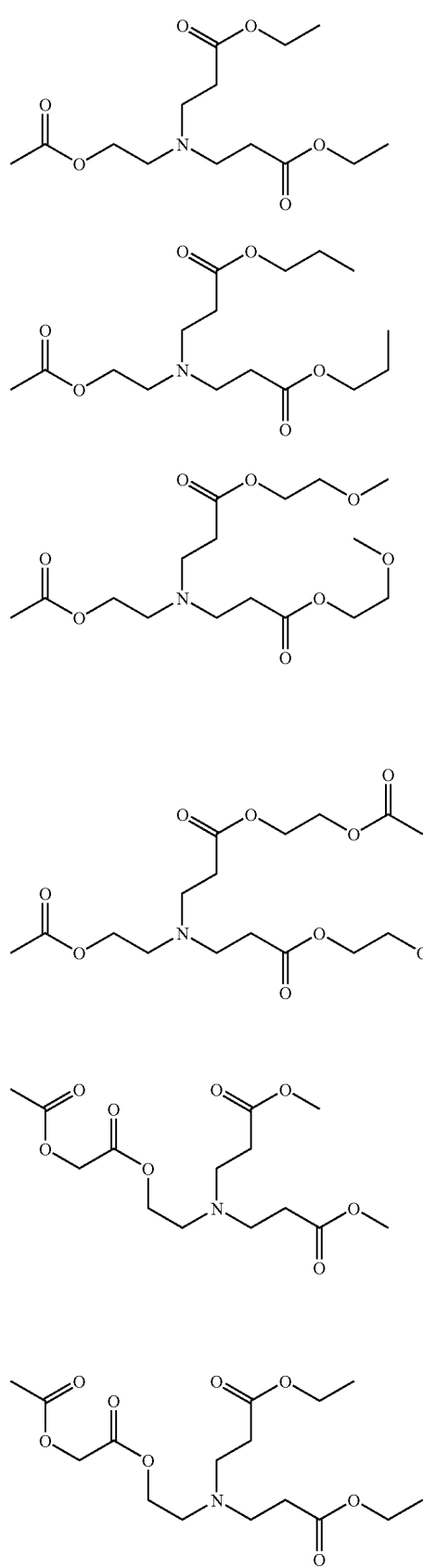
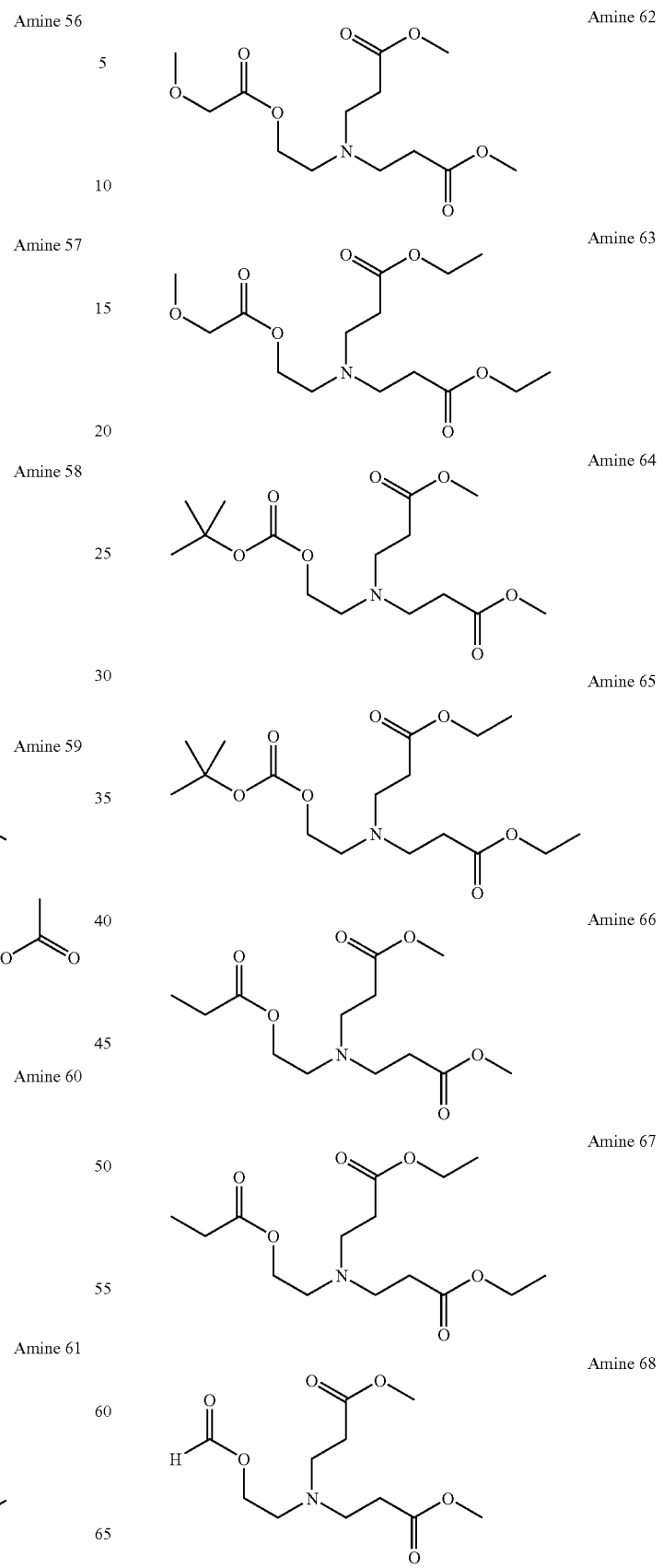

-continued

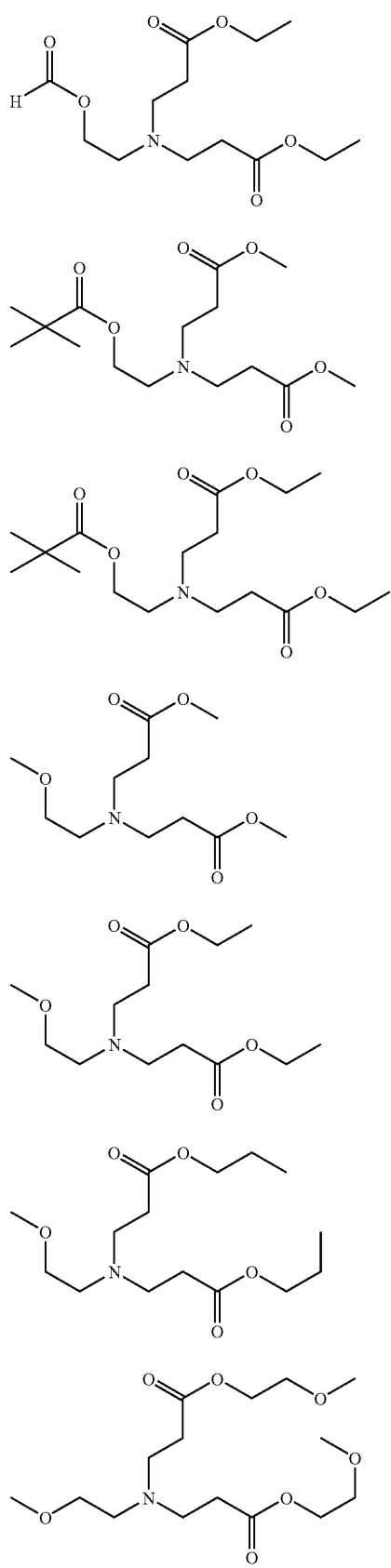

Amine 69
Amine 70
Amine 71
Amine 72
Amine 73
Amine 74
Amine 75

-continued

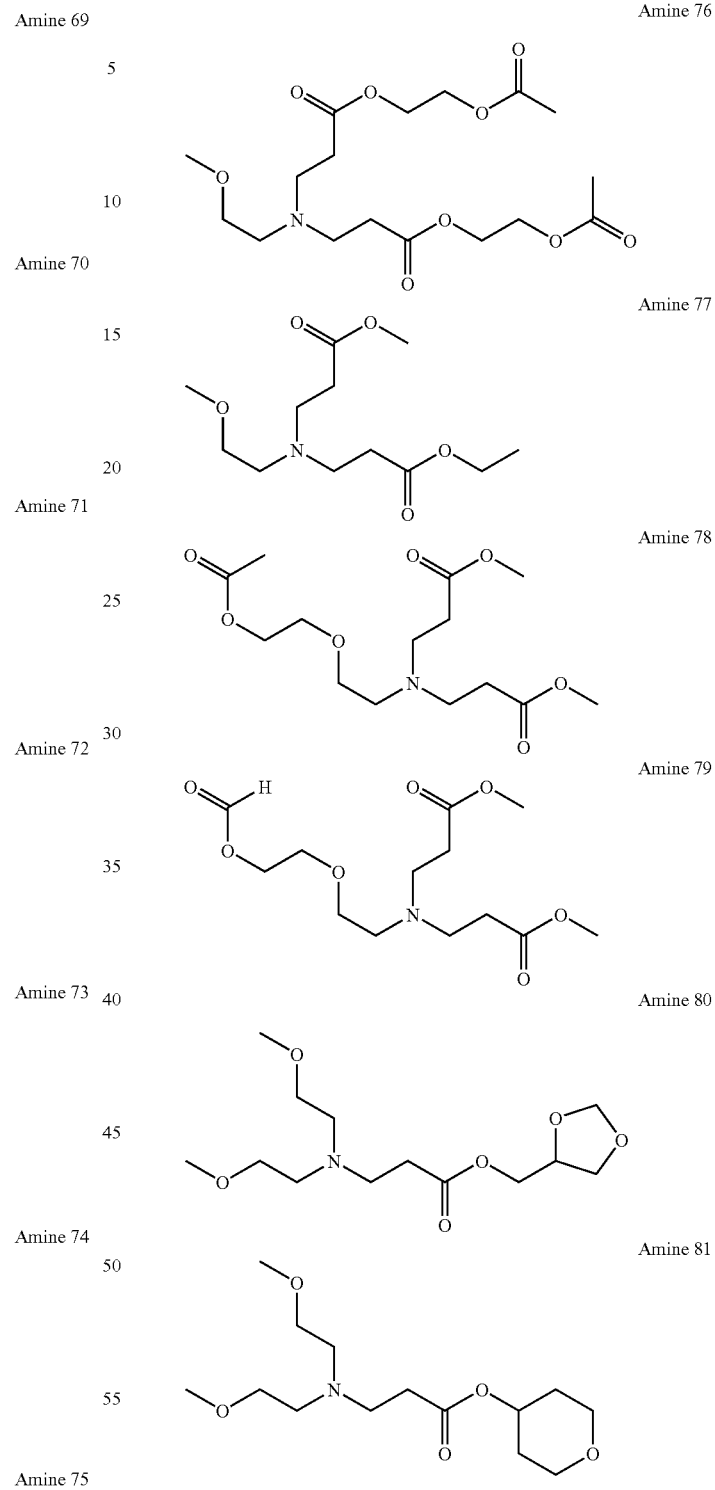

Amine 76
Amine 77
Amine 78
Amine 79
Amine 80
Amine 81

According to the present invention, it is believed that, in these ester group-containing tertiary amine compounds, an ester group and other oxygen-containing functional group having a high affinity for acids can be located at an appropriate position in the vicinity of the amine nitrogen atom so as to realize a high reaction rate with acids, and photoresists having these tertiary amine compounds added thereto can hence achieve a high resolution and a wide focus margin. Moreover, it is also believed that their basicity, reaction rate with acids, and diffusion rate in the resist can be properly controlled by selecting the most suitable combination of $R^1$ and $R^2$ in the general formula (1), making it possible to provide amine additives suitable for a wide variety of resist polymers and acid generators.

The ester group-containing tertiary amine compounds of the present invention, which are represented by the general formula (1), may be prepared, for example, by selecting the most suitable process from among the following processes according to the structure of the desired compound. However, it is to be understood that the present invention is not limited thereto. Now, these preparation processes are specifically described below.

As a first process, they may be synthesized in one step from a primary or secondary amine compound and an acrylic ester compound by utilizing the Michael addition reaction of an amine.

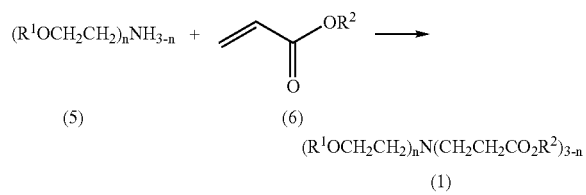

wherein n is 1 or 2; and $R^1$ and $R^2$ each independently represents a straight-chain, branched or cyclic alkyl group of 1 to 20 carbon atoms which may contain an ether, carbonyl or carbonyloxy group.

As to the amount of acrylic ester compound (6) used, it is desirable that, where the amine compound is a primary amine (i.e., n=1), the acrylic ester compound is used in an amount of 1.0 to 10 moles, preferably 1.6 to 2.4 moles, per mole of the amine compound (5), and where the amine compound is a secondary amine (i.e., n=2), the acrylic ester compound is used in an amount of 0.5 to 5.0 moles, preferably 0.8 to 1.2 moles, per mole of the amine compound (5). The reaction may be carried out in the absence or presence of a solvent.

Usable solvents include alcohols such as methanol, ethanol, isoproyl alcohol, t-butyl alcohol and ethylene glycol; hydrocarbons such as hexane, heptane, benzene, toluene and xylene; ethers such as diethyl ether, dibutyl ether, tetrahydrofuran, 1,4-dioxane and diglyme; chlorine-containing solvents such as methylene chloride, chloroform and 1,2-dichloroethylene; aprotic polar solvents such as N,N-dimethylformamide, N,N-dimethylacetamide, dimethyl sulfoxide and N-methylpyrrolidone; carboxylic acids such as formic acid and acetic acid; esters such as ethyl acetate and butyl acetate; ketones such as acetone and 2-butanone; nitrites such as acetonitrile; amines such as pyridine and triethylamine; and water. Suitable solvents may be selected from the foregoing ones according to the reaction conditions and used either alone or in admixture.

The reaction temperature may range from 0° C. to the reflux temperature of the solvent and may be determined according to the desired reaction rate. In order to enhance the reaction rate, there may be added a catalyst selected from inorganic acids such as hydrochloric acid, sulfuric acid and nitric acid, and salts thereof; and organic acids such as p-toluenesulfonic acid, formic acid, acetic acid, oxalic acid and trifluroacetic acid, and salts thereof. Moreover, in order to prevent the polymerization of the acrylic ester compound, a polymerization inhibitor such as hydroquinone, p-methoxyphenol, benzoquinone or phenylenediamine may be added. As to the reaction time, it is desirable from the viewpoint of yield to bring the reaction to completion while tracing it by gas chromatography (GC) or thin-layer chromatography (TLC). However, the reaction time usually ranges from about 2 to about 200 hours. The desired ester group-containing tertiary amine compound (1) can be obtained by concentrating the reaction mixture under reduced pressure, either directly or after being subjected to an ordinary aqueous work-up. If necessary, the ester group-containing tertiary amine compound thus obtained may further be purified according to common techniques such as distillation, chromatography and recrystallization.

As a second process, they may be synthesized from 2-aminoethanol or diethanolamine and an acrylic ester compound by two-step reactions comprising the Michael addition reaction of an amine (first step) and the acylation or alkylation of a hydroxyl group (second step).

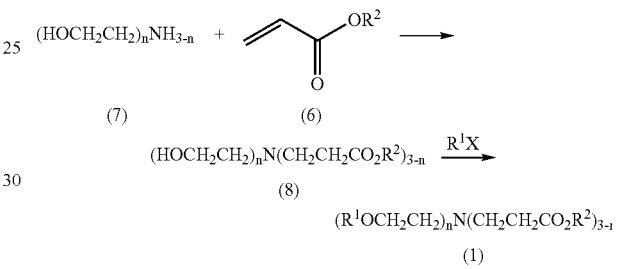

wherein n is 1 or 2; $R^1$ and $R^2$ each independently represents a straight-chain, branched or cyclic alkyl group of 1 to 20 carbon atoms which may contain an ether, carbonyl or carbonyloxy group; and X represents a leaving group such as halogen, alkylsulfonyloxy, acyloxy, hydroxyl or aryloxy.

In the reaction of the first step, it is desirable that, where the amine compound is 2-ethanolamine (i.e., n=1), the acrylic ester compound (6) is used in an amount of 1.0 to 10 moles, preferably 1.6 to 2.4 moles, per mole of the amine compound (7), and where the amine compound is diethanolamine (i.e., n=2), the acrylic ester compound is used in an amount of 0.5 to 5.0 moles, preferably 0.8 to 1.2 moles, per mole of the amine compound (7). The reaction may be carried out in the absence or presence of a solvent.

Usable solvents include alcohols such as methanol, ethanol, isoproyl alcohol, t-butyl alcohol and ethylene glycol; hydrocarbons such as hexane, heptane, benzene, toluene and xylene; ethers such as diethyl ether, dibutyl ether, tetrahydrofuran, 1,4-dioxane and diglyme; chlorine-containing solvents such as methylene chloride, chloroform and 1,2-dichloroethylene; aprotic polar solvents such as N,N-dimethylformamide, N,N-dimethylacetamide, dimethyl sulfoxide and N-methylpyrrolidone; carboxylic acids such as formic acid and acetic acid; esters such as ethyl acetate and butyl acetate; ketones such as acetone and 2-butanone; nitrites such as acetonitrile; amines such as pyridine and triethylamine; and water. Suitable solvents may be selected from the foregoing ones according to the reaction conditions and used either alone or in admixture. However, it is preferable from the viewpoint of efficiency to use the same solvent as used for the reaction of the next step, because the solvent need not be replaced.

The reaction temperature may range from 0° C. to the reflux temperature of the solvent and may be determined according to the desired reaction rate. In order to enhance the reaction rate, there may be added a catalyst selected from inorganic acids such as hydrochloric acid, sulfuric acid and nitric acid, and salts thereof; and organic acids such as p-toluenesulfonic acid, formic acid, acetic acid, oxalic acid and trifluroacetic acid, and salts thereof. Moreover, in order to prevent the polymerization of the acrylic ester compound, a polymerization inhibitor such as hydroquinone, p-methoxyphenol, benzoquinone or phenylenediamine may be added. As to the reaction time, it is desirable from the viewpoint of yield to bring the reaction to completion while tracing it by gas chromatography (GC) or thin-layer chromatography (TLC). However, the reaction time usually ranges from about 2 to about 200 hours. When the reaction is carried out in the absence of solvent or in the presence of the same solvent as used for the next step, the reaction of the next step may be continuously carried out in the same reaction vessel. Alternatively, the aminoalcohol compound (8) may be obtained as an intermediate product by concentrating the reaction mixture under reduced pressure, either directly or after being subjected to an ordinary aqueous work-up. If necessary, the aminoalcohol compound (8) thus obtained may further be purified according to common techniques such as distillation, chromatography and recrystallization. However, if the crude product has a sufficiently high purity, it may be directly used for the reaction of the second step.

In the reaction of the second step, where $R^1$ is an alkyl group, specific examples of $R^1X$ include, but are not limited to, methyl iodide, butyl bromide, dimethyl sulfate, ethyl iodide, diethyl sulfate, methoxymethyl chloride, (2-methoxyethoxy)methyl chloride, methyl chloroacetate and chloroacetone. Where $R^1$ is an acyl group, specific examples of $R^1X$ include, but are not limited to, formic acid, acetic formic anhydride, acetic anhydride, acetyl chloride, propionic anhydride, propionyl chloride, butyryl chloride, isobutyryl chloride, valeryl chloride, pivaloyl chloride, methoxyacetyl chloride, acetoxyacetyl chloride, di-t-butyl pyrocarbonate, phenyl acetate, p-nitrophenyl acetate and 2,4,6-trichlorophenyl acetate. As to the amount of $R^1X$ used, it is desirable that, where n=1, $R^1X$ is used in an amount of 0.5 to 5.0 moles, preferably 1.0 to 2.5 moles, per mole of the aminoalcohol compound (8), and where n=2, $R^1X$ is used in an amount of 1.0 to 10 moles, preferably 2.0 to 5.0 moles, per mole of the aminoalcohol compound (8). The reaction may be carried out in the absence or presence of a solvent.

Usable solvents include hydrocarbons such as hexane, heptane, benzene, toluene and xylene; ethers such as diethyl ether, dibutyl ether, tetrahydrofuran, 1,4-dioxane and diglyme; chlorine-containing solvents such as methylene chloride, chloroform and 1,2-dichloroethylene; aprotic polar solvents such as N,N-dimethylformamide, N,N-dimethylacetamide, dimethyl sulfoxide and N-methylpyrrolidone; carboxylic acids such as formic acid and acetic acid; esters such as ethyl acetate and butyl acetate; ketones such as acetone and 2-butanone; nitrites such as acetonitrile; and amines such as pyridine and triethylamine. Suitable solvents may be selected from the foregoing ones according to the reaction conditions and used either alone or in admixture.

A basic compound may be added in order to accelerate the reaction. Specific examples thereof include, but are not limited to, alkali metal or alkaline earth metal salts such as sodium hydroxide, potassium hydroxide, potassium carbonate, sodium carbonate, sodium bicarbonate, sodium hydride, calcium hydride, potassium t-butoxide and lithium t-butoxide; organometallic compounds such as n-butyl lithium, lithium diisopropylamide, lithium hexamethyldisilazide and bromomagensium diisopropylamide; and organic amines such as pyridine, triethylamine, diisopropylethylamine, N,N-dimethylaniline and 4-dimethylaminopyridine. These basic compounds may be used either alone or in admixture of two or more. They are preferably be used in an amount of 0.8 to 10 moles, more preferably 0.9 to 3.0 moles, per mole of $R^1X$.

The reaction temperature may range from −70° C. to the reflux temperature of the solvent. However, it is preferable to use a reaction temperature in the range of 0 to 50° C. As to the reaction time, it is desirable from the viewpoint of yield to bring the reaction to completion while tracing it by gas chromatography (GC) or thin-layer chromatography (TLC). However, the reaction time usually ranges from about 0.2 to about 20 hours. The desired ester group-containing tertiary amine compound (1) can be obtained by subjecting the reaction mixture to an ordinary aqueous work-up. If necessary, the compound (1) may further be purified according to common techniques such as distillation, chromatography and recrystallization.

Finally, as a third process, they may be synthesized by subjecting another ester group-containing tertiary amine compound of the present invention to an ester exchange reaction with an alcohol in the presence of a catalyst.

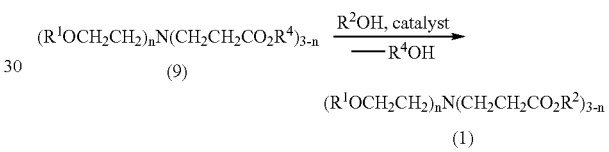

wherein n is 1 or 2; $R^1$ and $R^2$ each independently represents a straight-chain, branched or cyclic alkyl group of 1 to 20 carbon atoms which may contain an ether, carbonyl or carbonyloxy group; and $R^4$ represents a lower alkyl group such as methyl, ethyl, propyl or butyl.

In this reaction, the desired compound (1) is obtained by using an ester group-containing tertiary amine compound (9) prepared by the above-described first or second process as a starting material and subjecting it to an ester exchange reaction with an alcohol ($R^2OH$) in the presence of a catalyst. This reaction may be carried out in the absence or presence of a solvent. In order to enhance efficiency and shorten the reaction time, it is preferable to carry out the reaction while distilling off the alcohol ($R^4OH$) newly formed by the reaction. It is desirable that the alcohol ($R^2OH$) is used in an amount of 0.5 to 5.0 moles, preferably 1.0 to 1.5 moles, per mole of the ester group-containing tertiary amine compound (9).

Usable ester exchange catalysts include, but are not limited to, organic amines such as triethylamine, 1,8-diazabicyclo[5.4.0]-7-undecene and 4-dimethylaminopyridine; inorganic bases such as sodium hydroxide, potassium carbonate and sodium carbonate; metal alkoxides such as sodium methoxide, potassium t-butoxide, magnesium ethoxide and titanium(IV) methoxide; salts such as iron(III) sulfate and calcium chloride; and inorganic or organic acids such as hydrogen chloride, sulfuric acid and p-toluenesulfonic acid. It is desirable that the ester exchange catalyst is used in an amount of 0.001 to 5.0 moles, preferably 0.001 to 0.1 moles, per mole of the ester group-containing tertiary amine compound (9).

Usable solvents include ethers such as tetrahydrofuran, di-n-butyl ether and 1,4-dioxane; hydrocarbons such as n-hexane, n-heptane, benzene, toluene, xylene and cumene; and chlorine-containing solvents such as chloroform and dichloroethylene. Suitable solvents may be selected from the foregoing ones and used either alone or in admixture.

Although the reaction temperature may vary according to the reaction conditions, it preferably ranges from 50° C. to 200° C. It is especially preferable to carry out the reaction at a temperature close to the boiling point of the reaction solvent while distilling off the alcohol ($R^4OH$) formed. As to the reaction time, it is desirable from the viewpoint of yield to bring the reaction to completion while tracing it by gas chromatography (GC) or thin-layer chromatography (TLC). However, the reaction time usually ranges from about 1 to about 20 hours. The desired ester group-containing tertiary amine compound (1) may be obtained subjecting the reaction mixture to an ordinary aqueous work-up. If necessary, the compound (1) may further be purified according to common techniques such as distillation, chromatography and recrystallization. Alternatively, the desired compound (1) may be obtained by distilling the reaction mixture directly.

The ester group-containing tertiary amine compounds of the present invention which have been prepared in the above-described manner may be added to chemically amplified resists, either alone or in admixture of two or more, so that they produce an excellent effect in preventing a film loss, enhancing the resolution, and extending the focus margin, regardless of exposure wavelength. In particular, they can be suitably used in KrF resists, ArF resists, $F_2$ resists and EB resists.

The resist materials containing the ester group-containing tertiary amine compounds of the present invention may generally be prepared by compounding a resist base polymer, a photochemical acid generator, an organic solvent, and an ester group-containing tertiary amine compound in accordance with the present invention. If necessary, another type of basic compound, a crosslinker, a dissolution inhibitor and the like may also be added thereto. These resist materials may be prepared in the usual manner.

The ester group-containing tertiary amine compound of the present invention is preferably added in an amount of 0.001 to 2.0 parts by weight, more preferably 0.01 to 1.0 part by weight, per 100 parts by weight of the total base resin. If its amount added is less than 0.001 part by weight, its addition may fail to produce an appreciable effect, and if its amount added is greater than 2 parts by weight, the resulting resist material may show an undue reduction in sensitivity.

The present invention is more specifically explained with reference to the following synthesis examples, reference examples and comparative reference examples. However, these examples are not to be construed to limit the scope of the invention.

SYNTHESIS EXAMPLES

Among the ester group-containing tertiary amine compounds of the present invention, the aforesaid amines 1–81 were synthesized according to the formulations described below.

Synthesis Example 1

Synthesis of Amine 1

10.5 g of ethyl acrylate was added to 10.5 g of diethanolamine at 20–30° C., and the resulting mixture was allowed to stand for 20 hours. After 25.6 g of triethylamine, 100 mg of 4-dimethylaminopyridine, and 100 g of THF were added thereto, 22.4 g of acetic anhydride was added thereto at 20–30° C., followed by stirring for 10 hours. After the reaction was stopped by the addition of water, the reaction mixture was extracted with ethyl acetate. The organic layer was washed with water, dried over anhydrous sodium sulfate, and concentrated under reduced pressure to obtain 27.5 g (95% yield) of amine 1.

Synthesis Example 2

Synthesis of Amine 2

Amine 2 was synthesized (in a 96% yield) in the same manner as in Synthesis Example 1, except that propyl acrylate was used in place of ethyl acrylate.

Synthesis Example 3

Synthesis of Amine 3

Amine 3 was synthesized (in a 94% yield) in the same manner as in Synthesis Example 1, except that isopropyl acrylate was used in place of ethyl acrylate.

Synthesis Example 4

Synthesis of Amine 4

Amine 4 was synthesized (in a 94% yield) in the same manner as in Synthesis Example 1, except that butyl acrylate was used in place of ethyl acrylate.

Synthesis Example 5

Synthesis of Amine 5

Amine 5 was synthesized (in a 93% yield) in the same manner as in Synthesis Example 1, except that pentyl acrylate was used in place of ethyl acrylate.

Synthesis Example 6

Synthesis of Amine 6

Amine 6 was synthesized (in a 95% yield) in the same manner as in Synthesis Example 1, except that hexyl acrylate was used in place of ethyl acrylate.

Synthesis Example 7

Synthesis of Amine 7

Amine 7 was synthesized (in a 92% yield) in the same manner as in Synthesis Example 1, except that cyclohexyl acrylate was used in place of ethyl acrylate.

Synthesis Example 8

Synthesis of Amine 8

Amine 8 was synthesized (in a 90% yield) in the same manner as in Synthesis Example 1, except that decyl acrylate was used in place of ethyl acrylate.

Synthesis Example 9

Synthesis of Amine 9

Amine 9 was synthesized (in a 88% yield) in the same manner as in Synthesis Example 1, except that pentadecyl acrylate was used in place of ethyl acrylate.

Synthesis Example 10

Synthesis of Amine 10

Amine 10 was synthesized (in a 85% yield) in the same manner as in Synthesis Example 1, except that dodecyl acrylate was used in place of ethyl acrylate.

Synthesis Example 11

Synthesis of Amine 11

11.6 g of 2-hydroxyethyl acrylate was added to 10.5 g of diethanolamine at 20–30° C., and the resulting mixture was allowed to stand for 20 hours. After 38.4 g of triethylamine, 150 mg of 4-dimethylaminopyridine, and 100 g of THF were added thereto, 33.6 g of acetic anhydride was added thereto at 20–30° C., followed by stirring for 10 hours. After the reaction was stopped by the addition of water, the reaction mixture was extracted with ethyl acetate. The organic layer was washed with water, dried over anhydrous sodium sulfate, and concentrated under reduced pressure. The resulting residue was purified by vacuum distillation to obtain 31.3 g (90% yield) of amine 11 (boiling point 164–166° C./27 Pa).

IR (thin film): $\nu$=2960, 2837, 1740, 1443, 1375, 1236, 1190, 1043 $cm^{-1}$.

$^1$H-NMR (300 MHz in $CDCl_3$): $\delta$=2.02 (6H, s), 2.05 (3H, s), 2.45 (2H, t, J=6.9 Hz), 2.75 (4H, t, J=6.1 Hz), 2.88 (2H, t, J=6.9 Hz), 4.08 (4H, t, J=6.1 Hz), 4.25 (4H, s).

Synthesis Example 12

Synthesis of Amine 12

Amine 12 was synthesized (in a 86% yield) in the same manner as in Synthesis Example 1, except that 2-methoxyethyl acrylate was used in place of ethyl acrylate. Boiling point 146–148° C./9.3 Pa.

IR (thin film): $\nu$=2954, 2893, 2825, 1738, 1456, 1371, 1238, 1198, 1130, 1039 $cm^{-1}$.

$^1$H-NMR (300 MHz in $CDCl_3$): $\delta$=2.02 (6H, s), 2.46 (2H, t, J=7.1 Hz), 2.74 (4H, t, J=6.0 Hz), 2.88 (2H, t, J=7.1 Hz), 3.36 (3H, s), 3.56 (2H, m), 4.08 (4H, t, J=6.0 Hz), 4.20 (2H, m).

Synthesis Example 13

Synthesis of Amine 13

Amine 13 was synthesized (in a 70% yield) in the same manner as in Synthesis Example 1, except that 2-oxotetrahydrofuran-3-yl acrylate was used in place of ethyl acrylate.

IR (thin film): $\nu$=2962, 2837, 1792, 1743, 1668, 1456, 1437, 1373, 1240, 1196, 1095, 1043 $cm^{-1}$.

Synthesis Example 14

Synthesis of Amine 14

Amine 14 was synthesized (in a 60% yield) in the same manner as in Synthesis Example 1, except that (methoxycarbonyl)methyl acrylate was used in place of ethyl acrylate. Boiling point 154–157° C./17 Pa.

IR (thin film): $\nu$=2956, 2837, 1740, 1439, 1377, 1236, 1180, 1041 $cm^{-1}$.

$^1$H-NMR (300 MHz in $CDCl_3$): $\delta$=2.02 (6H, s), 2.54 (2H, t, J=7.1 Hz), 2.76 (4H, t, J=5.9 Hz), 2.92 (2H, t, J=7.1 Hz), 3.74 (3H, s), 4.09 (4H, t, J=5.9 Hz), 4.59 (2H, s).

Synthesis Example 15

Synthesis of Amine 15

Amine 15 was synthesized (in a 85% yield) in the same manner as in Synthesis Example 1, except that 2-oxopropyl acrylate was used in place of ethyl acrylate. Boiling point 165° C./27 Pa.

IR (thin film): $\nu$=2960, 2837, 1736, 1421, 1373, 1238, 1174, 1041 $cm^{-1}$.

$^1$H-NMR (300 MHz in $CDCl_3$): $\delta$=2.02 (6H, s), 2.13 (3H, s), 2.55 (2H, t, J=7.1 Hz), 2.76 (4H, t, J=5.9 Hz), 2.92 (2H, t, J=7.1 Hz), 4.08 (4H, t, J=5.9 Hz), 4.63 (2H, s).

Synthesis Example 16

Synthesis of Amine 16

Amine 16 was synthesized (in a 76% yield) in the same manner as in Synthesis Example 1, except that tetrahydrofurfuryl acrylate was used in place of ethyl acrylate. Boiling point 165° C./20 Pa.

IR (thin film): $\nu$=2958, 2873, 1740, 1450, 1371, 1238, 1193, 1039 $cm^{-1}$.

$^1$H-NMR (300 MHz in $CDCl_3$): $\delta$=0.56 (1H, m), 1.80–2.10 [10H, m including 2.02 (6H, s)], 2.47 (2H, t, J=7.1 Hz), 2.74 (4H, t, J=6.0 Hz), 2.88 (2H, t, J=7.1 Hz), 3.70–4.20 [9H, m including 4.06 (4H, t, J=6.0 Hz)].

Synthesis Example 17

Synthesis of Amine 17

Amine 17 was synthesized (in a 88% yield) in the same manner as in Synthesis Example 1, except that 2-(2-methoxyethoxy)ethyl acrylate was used in place of ethyl acrylate.

Synthesis Example 18

Synthesis of Amine 18

Amine 18 was synthesized (in a 90% yield) in the same manner as in Synthesis Example 1, except that 2-ethoxyethyl acrylate was used in place of ethyl acrylate.

Synthesis Example 19

Synthesis of Amine 19

Amine 19 was synthesized (in a 87% yield) in the same manner as in Synthesis Example 11, except that 4-hydroxybutyl acrylate was used in place of 2-hydroxyethyl acrylate.

Synthesis Example 20

Synthesis of Amine 20

Amine 20 was synthesized (in a 80% yield) in the same manner as in Synthesis Example 1, except that methyl acrylate was used in place of ethyl acrylate and acetoxyacetyl chloride was used in place of acetic anhydrate.

Synthesis Example 21

Synthesis of Amine 21

Amine 21 was synthesized (in a 78% yield) in the same manner as in Synthesis Example 1, except that acetoxyacetyl chloride was used in place of acetic anhydride.

Synthesis Example 22

Synthesis of Amine 22

Amine 22 was synthesized (in a 82% yield) in the same manner as in Synthesis Example 1, except that methyl acrylate was used in place of ethyl acrylate, and methoxyacetyl chloride in place of acetic anhydride.

Synthesis Example 23

Synthesis of Amine 23

Amine 23 was synthesized (in a 80% yield) in the same manner as in Synthesis Example 1, except that methoxyacetyl chloride was used in place of acetic anhydride.

Synthesis Example 24

Synthesis of Amine 24

Amine 24 was synthesized (in a 85% yield) in the same manner as in Synthesis Example 1, except that methyl acrylate was used in place of ethyl acrylate, and di-t-butyl pyrocarbonate in place of acetic anhydride.

Synthesis Example 25

Synthesis of Amine 25

Amine 25 was synthesized (in a 80% yield) in the same manner as in Synthesis Example 1, except that di-t-butyl pyrocarbonate was used in place of acetic anhydride.

Synthesis Example 26

Synthesis of Amine 26

Amine 26 was synthesized (in a 82% yield) in the same manner as in Synthesis Example 1, except that methyl acrylate was used in place of ethyl acrylate, and propionyl chloride in place of acetic anhydride.

Synthesis Example 27

Synthesis of Amine 27

Amine 27 was synthesized (in a 81% yield) in the same manner as in Synthesis Example 1, except that propionyl chloride was used in place of acetic anhydride.

Synthesis Example 28

Synthesis of Amine 28

8.6 g of methyl acrylate was added to 10.5 g of diethanolamine at 20–30° C., and the resulting mixture was allowed to stand for 20 hours. Then, 100 g of formic acid was added thereto, followed by stirring at 80° C. for 20 hours. After the reaction mixture was diluted with ethyl acetate, it was neutralized by the addition of a 5% aqueous solution of sodium bicarbonate, washed with water, dried over anhydrous sodium sulfate, and concentrated under reduced pressure to obtain 19.8 g (80% yield) of amine 28.

Synthesis Example 29

Synthesis of Amine 29

Amine 29 was synthesized (in a 81% yield) in the same manner as in Synthesis Example 28, except that ethyl acrylate was used in place of methyl acrylate.

Synthesis Example 30

Synthesis of Amine 30

Amine 30 was synthesized (in a 40% yield) in the same manner as in Synthesis Example 28, except that 2-hydroxyethyl acrylate was used in place of methyl acrylate.

IR (thin film): ν=2956, 2839, 1722, 1456, 1275, 1254, 1173, 1061 cm$^{-1}$.

$^1$H-NMR (270 MHz in CDCl$_3$): δ=2.47 (2H, t, J=7.0 Hz), 2.80 (4H, t, J=5.9 Hz), 2.90 (2H, t, J=7.0 Hz), 4.19 (4H, t, J=5.9 Hz), 4.25–4.40 (4H, m), 8.03 (2H, s), 8.06 (1H, s).

Synthesis Example 31

Synthesis of Amine 31

Amine 31 was synthesized (in a 70% yield) in the same manner as in Synthesis Example 28, except that 4-hydroxybutyl acrylate was used in place of methyl acrylate.

IR (thin film): ν=2960, 2839, 1722, 1466, 1363, 1254, 1176, 1065 cm$^{-1}$.

$^1$H-NMR (270 MHz in CDCl$_3$): δ=1.65–1.80 (4H, m), 2.44 (2H, t, J=7.2 Hz), 2.80 (4H, t, J=5.8 Hz), 2.89 (2H, t, J=7.2 Hz), 4.05–4.25 (8H, m), 8.03 (2H, s), 8.04 (1H, s).

Synthesis Example 32

Synthesis of Amine 32

Amine 32 was synthesized (in a 81% yield) in the same manner as in Synthesis Example 1, except that methyl acrylate was used in place of ethyl acrylate, and pivaloyl chloride in place of acetic anhydride.

Synthesis Example 33

Synthesis of Amine 33

Amine 33 was synthesized (in a 80% yield) in the same manner as in Synthesis Example 1, except that pivaloyl chloride was used in place of acetic anhydride.

Synthesis Example 34

Synthesis of Amine 34

13.3 g of bis(2-methoxyethyl)amine was added to a mixture of 10.0 g of methyl acrylate and 10.0 g of methanol at 20–30° C., and the resulting mixture was allowed to stand for 200 hours. The reaction mixture was concentrated under reduced pressure and then purified by vacuum distillation to obtain 215 g (98% yield) of amine 34 (boiling point 71–75° C./27 Pa).

IR (thin film): $\nu$=2951, 2927, 2877, 2818, 1740, 1437, 1254, 1198, 1119 cm$^{-1}$.

$^1$H-NMR (270 MHz in CDCl$_3$): $\delta$=2.46 (2H, t, J=7.3 Hz), 2.69 (4H, t, J=6.0 Hz), 2.89 (2H, t, J=7.3 Hz), 3.31 (6H, s), 3.43 (4H, t, J=6.0 Hz), 3.64 (3H, s).

Synthesis Example 35

Synthesis of Amine 35

Amine 35 was synthesized (in a 90% yield) in the same manner as in Synthesis Example 34, except that ethyl acrylate was used in place of methyl acrylate (boiling point 74° C./16 Pa).

IR (thin film): $\nu$=2980, 2929, 2875, 2816, 1734, 1458, 1369, 1302, 1252, 1188, 1120, 1049 cm$^{-1}$.

$^1$H-NMR (300 MHz in CDCl$_3$): $\delta$=1.21 (3H, t, J=7.2 Hz), 2.42 (2H, t, J=6.0 Hz), 2.67 (4H, t, J=6.2 Hz), 2.86 (2H, t, J=6.0 Hz), 3.29 (6H, s), 3.41 (4H, t, J=6.2 Hz), 4.08 (2H, q, J=7.2 Hz).

Synthesis Example 36

Synthesis of Amine 36

Amine 36 was synthesized (in a 89% yield) in the same manner as in Synthesis Example 34, except that propyl acrylate was used in place of methyl acrylate.

Synthesis Example 37

Synthesis of Amine 37

Amine 37 was synthesized (in a 90% yield) in the same manner as in Synthesis Example 34, except that butyl acrylate was used in place of methyl acrylate.

Synthesis Example 38

Synthesis of Amine 38

Amine 38 was synthesized (in a 88% yield) in the same manner as in Synthesis Example 34, except that pentyl acrylate was used in place of methyl acrylate.

Synthesis Example 39

Synthesis of Amine 39

Amine 39 was synthesized (in a 87% yield) in the same manner as in Synthesis Example 34, except that hexyl acrylate was used in place of methyl acrylate. Boiling point 121° C./16 Pa.

IR (thin film): $\nu$=2956, 2929, 2873, 2816, 1736, 1460, 1248, 1184, 1120, 1068, 1012 cm$^{-1}$.

$^1$H-NMR (300 MHz in CDCl$_3$): $\delta$=0.87 (3H, m), 1.20–1.40 (6H, m), 1.59 (2H, m), 2.45 (2H, t, J=7.2 Hz), 2.70 (4H, t, J=5.9 Hz), 2.89 (2H, t, J=7.2 Hz), 3.31 (6H, s), 3.44 (4H, t, J=5.9 Hz), 4.04 (2H, t, J=6.8 Hz).

Synthesis Example 40

Synthesis of Amine 40

Amine 40 was synthesized (in a 85% yield) in the same manner as in Synthesis Example 34, except that cyclohexyl acrylate was used in place of methyl acrylate.

Synthesis Example 41

Synthesis of Amine 41

Amine 41 was synthesized (in a 89% yield) in the same manner as in Synthesis Example 34, except that 2-ethylhexyl acrylate was used in place of methyl acrylate.

Synthesis Example 42

Synthesis of Amine 42

Amine 42 was synthesized (in a 90% yield) in the same manner as in Synthesis Example 34, except that 2-methoxyethyl acrylate was used in place of methyl acrylate.

Synthesis Example 43

Synthesis of Amine 43

Amine 43 was synthesized (in a 89% yield) in the same manner as in Synthesis Example 34, except that 2-ethoxyethyl acrylate was used in place of methyl acrylate.

Synthesis Example 44

Synthesis of Amine 44

Amine 44 was synthesized (in a 88% yield) in the same manner as in Synthesis Example 34, except that 2-propoxyethyl acrylate was used in place of methyl acrylate.

Synthesis Example 45

Synthesis of Amine 45

Amine 45 was synthesized (in a 87% yield) in the same manner as in Synthesis Example 34, except that 2-isopropoxyethyl acrylate was used in place of methyl acrylate.

Synthesis Example 46

Synthesis of Amine 46

Amine 46 was synthesized (in a 89% yield) in the same manner as in Synthesis Example 34, except that 2-butoxyethyl acrylate was used in place of methyl acrylate.

Synthesis Example 47

Synthesis of Amine 47

Amine 47 was synthesized (in a 91% yield) in the same manner as in Synthesis Example 34, except that 2-(2-methoxyethoxy)ethyl acrylate was used in place of methyl acrylate.

Synthesis Example 48

Synthesis of Amine 48

Amine 48 was synthesized (in a 70% yield) in the same manner as in Synthesis Example 34, except that tetrahydrofurfuryl acrylate was used in place of methyl acrylate (boiling point 130° C./14 Pa).

IR (thin film): ν=2976, 2947, 2929, 2875, 1736, 1458, 1389, 1363, 1250, 1184, 1119, 1078, 1024 cm$^{-1}$.

$^1$H-NMR (300 MHz in CDCl$_3$): δ=1.56 (1H, m), 1.75–2.05 (3H, m), 2.50 (2H, t, J=7.2 Hz), 2.69 (4H, t, J=6.0 Hz), 3.70–4.20 (5H, m).

Synthesis Example 49

Synthesis of Amine 49

Amine 49 was synthesized (in a 88% yield) in the same manner as in Synthesis Example 34, except that 2-oxopropyl acrylate was used in place of methyl acrylate.

Synthesis Example 50

Synthesis of Amine 50

Amine 50 was synthesized (in a 90% yield) in the same manner as in Synthesis Example 34, except that 2-acetoxyethyl acrylate was used in place of methyl acrylate.

Synthesis Example 51

Synthesis of Amine 51

Amine 51 was synthesized (in a 84% yield) in the same manner as in Synthesis Example 34, except that 4-acetoxybutyl acrylate was used in place of methyl acrylate. Boiling point 137° C./19 Pa.

IR (thin film): ν=2954, 2929, 2875, 2815, 1738, 1458, 1389, 1365, 1240, 1184, 1119, 1047 cm$^{-1}$.

$^1$H-NMR (300 MHz in CDCl$_3$): δ=1.68 (4H, m), 2.03 (3H, s), 2.46 (2H, br.t, J=7.3 Hz), 2.70 (4H, br.t, J=5.9 Hz), 2.89 (2H, br.t, J=7.3 Hz), 3.31 (6H, s), 2.43 (4H, br.t, J=5.9 Hz), 4.07 (4H, m).

Synthesis Example 52

Synthesis of Amine 52

Amine 52 was synthesized (in a 80% yield) in the same manner as in Synthesis Example 34, except that 2-(acetoxyacetoxy)ethyl acrylate was used in place of methyl acrylate.

Synthesis Example 53

Synthesis of Amine 53

Amine 53 was synthesized (in a 83% yield) in the same manner as in Synthesis Example 34, except that 2-(t-butoxycarbonyloxy)ethyl acrylate was used in place of methyl acrylate.

Synthesis Example 54

Synthesis of Amine 54

Amine 54 was synthesized (in a 79% yield) in the same manner as in Synthesis Example 34, except that 2-(methoxycarbonylmethoxy)ethyl acrylate was used in place of methyl acrylate.

Synthesis Example 55

Synthesis of Amine 55

17.5 g of methyl acrylate was added to 6.11 g of 2-aminoethanol at 20–30° C., and the resulting mixture was allowed to stand for 20 hours. Then, 12.1 g of triethylamine, 50 mg of 4-dimethylaminopyridine, and 50 g of THF were added thereto. Thereafter, 11.2 g of acetic anhydride was added thereto at 20–30° C., followed by stirring for 5 hours. After the reaction was stopped by the addition of water, the reaction mixture was extracted with ethyl acetate, the organic layer was washed with water, dried over anhydrous sodium sulfate, and concentrated under reduced pressure. The resulting residue was purified by vacuum distillation to obtain 26.2 g (95% yield) of amine 55 (boiling point 120° C./15 Pa).

IR (thin film): ν=2954, 2839, 1740, 1439, 1373, 1238, 1200, 1176, 1039 cm$^{-1}$.

$^1$H-NMR (300 MHz in CDCl$_3$): δ=2.01 (3H, s), 2.41 (4H, t, J=6.9 Hz), 2.67 (2H, t, J=6.0 Hz), 2.79 (4H, t, J=6.9 Hz), 3.63 (6H, s), 4.06 (2H, t, J=6.0 Hz).

Synthesis Example 56

Synthesis of Amine 56

Amine 56 was synthesized (in a 93% yield) in the same manner as in Synthesis Example 55, except that ethyl acrylate was used in place of methyl acrylate.

Synthesis Example 57

Synthesis of Amine 57

Amine 57 was synthesized (in a 91% yield) in the same manner as in Synthesis Example 55, except that propyl acrylate was used in place of methyl acrylate.

Synthesis Example 58

Synthesis of Amine 58

Amine 58 was synthesized (in a 90% yield) in the same manner as in Synthesis Example 55, except that 2-methoxyethyl acrylate was used in place of methyl acrylate.

Synthesis Example 59

Synthesis of Amine 59

Amine 59 was synthesized (in a 88% yield) in the same manner as in Synthesis Example 55, except that 2-acetoxyethyl acrylate was used in place of methyl acrylate.

Synthesis Example 60

Synthesis of Amine 60

Amine 60 was synthesized (in a 83% yield) in the same manner as in Synthesis Example 55, except that acetoxyacetyl chloride was used in place of acetic anhydride.

Synthesis Example 61

Synthesis of Amine 61

Amine 61 was synthesized (in a 82% yield) in the same manner as in Synthesis Example 55, except that ethyl acrylate was used in place of methyl acrylate, and acetoxyacetyl chloride in place of acetic anhydride.

Synthesis Example 62

Synthesis of Amine 62

Amine 62 was synthesized (in a 85% yield) in the same manner as in Synthesis Example 55, except that methoxyacetyl chloride was used in place of acetic anhydride.

Synthesis Example 63

Synthesis of Amine 63

Amine 63 was synthesized (in a 84% yield) in the same manner as in Synthesis Example 55, except that ethyl acrylate was used in place of methyl acrylate, and methoxyacetyl hloride in place of acetic anhydride.

Synthesis Example 64

Synthesis of Amine 64

Amine 64 was synthesized (in a 87% yield) in the same manner as in Synthesis Example 55, except that di-t-butyl pyrocarbonate was used in place of acetic anhydride.

Synthesis Example 65

Synthesis of Amine 65

Amine 65 was synthesized (in a 86% yield) in the same manner as in Synthesis Example 55, except that ethyl acrylate was used in place of methyl acrylate, and di-t-butyl pyrocarbonate in place of acetic anhydride.

Synthesis Example 66

Synthesis of Amine 66

Amine 66 was synthesized (in a 85% yield) in the same manner as in Synthesis Example 55, except that propionyl chloride was used in place of acetic anhydride.

Synthesis Example 67

Synthesis of Amine 67

Amine 67 was synthesized (in a 83% yield) in the same manner as in Synthesis Example 55, except that ethyl acrylate was used in place of methyl acrylate, and propionyl chloride in place of acetic anhydride.

Synthesis Example 68

Synthesis of Amine 68

17.5 g of methyl acrylate was added to 6.11 g of 2-aminoethanol at 20–30° C., and the resulting mixture was allowed to stand for 20 hours. Then, 100 g of formic acid was added thereto, followed by stirring at 80° C. for 20 hours. After the reaction mixture was diluted with ethyl acetate, it was neutralized with a 5% aqueous solution of sodium bicarbonate, washed with water, dried over anhydrous sodium sulfate, and concentrated under reduced pressure. The resulting residue was purified by vacuum distillation to obtain amine 68 (in a 75% yield).

Synthesis Example 69

Synthesis of Amine 69

Amine 69 was synthesized (in a 76% yield) in the same manner as in Synthesis Example 68, except that ethyl acrylate was used in place of methyl acrylate.

Synthesis Example 70

Synthesis of Amine 70

Amine 70 was synthesized (in a 83% yield) in the same manner as in Synthesis Example 55, except that pivaloyl chloride was used in place of acetic anhydride.

Synthesis Example 71

Synthesis of Amine 71

Amine 71 was synthesized (in a 82% yield) in the same manner as in Synthesis Example 55, except that ethyl acrylate was used in place of methyl acrylate, and pivaloyl chloride in place of acetic anhydride.

Synthesis Example 72

Synthesis of Amine 72

7.5 g of 2-methoxyethylamine was added to a mixture of 20.0 g of methyl acrylate and 10.0 g of methanol at 20–30° C., and the resulting mixture was allowed to stand for 200 hours. The reaction mixture was concentrated under reduced pressure and then purified by vacuum distillation to obtain 23.5 g (95% yield) of amine 72 (boiling point 81–85° C./27 Pa).

IR (thin film): $\nu$=2953, 2839, 1740, 1437, 1255, 1200, 1176, 1119 cm$^{-1}$.

$^1$H-NMR (270 MHz in CDCl$_3$): $\delta$=2.44 (4H, t, J=7.2 Hz), 2.63 (2H, t, J=6.1 Hz), 2.81 (4H, t, J=7.2 Hz), 3.31 (3H, s), 3.41 (2H, t, J=6.1 Hz), 3.64 (6H, s).

Synthesis Example 73

Synthesis of Amine 73

Amine 73 was synthesized (in a 93% yield) in the same manner as in Synthesis Example 72, except that ethyl acrylate was used in place of methyl acrylate (boiling point 120° C./80 Pa).

IR (thin film): $\nu$=2981, 2933, 2875, 2825, 1734, 1464, 1371, 1302, 1254, 1182, 1119, 1045 cm$^{-1}$.

¹H-NMR (300 MHz in CDCl$_3$): δ=1.23 (6H, t, J=7.1 Hz), 2.42 (4H, t, J=7.2 Hz), 2.63 (2H, t, J=6.2 Hz), 2.81 (4H, t, J=7.2 Hz), 3.31 (3H, s), 3.41 (2H, t, J=6.2 Hz), 4.09 (4H, q, J=7.1 Hz).

Synthesis Example 74

Synthesis of Amine 74

Amine 74 was synthesized (in a 91% yield) in the same manner as in Synthesis Example 72, except that propyl acrylate was used in place of methyl acrylate.

Synthesis Example 75

Synthesis of Amine 75

Amine 75 was synthesized (in a 91% yield) in the same manner as in Synthesis Example 72, except that 2-methoxyethyl acrylate was used in place of methyl acrylate.

Synthesis Example 76

Synthesis of Amine 76

Amine 76 was synthesized (in a 85% yield) in the same manner as in Synthesis Example 72, except that 2-acetoxyethyl acrylate was used in place of methyl acrylate.

Synthesis Example 77

Synthesis of Amine 77

8.6 g of methyl acrylate was added to 7.5 g of 2-methoxyethylamine at 20–30° C., and the resulting mixture was stirred for 10 hours. Then, 15.0 g of ethyl acrylate was added thereto, followed by stirring for 200 hours. The react ion mixture was concentrated under reduced pressure to obtain amine 77 (in a 97% yield).

Synthesis Example 78

Synthesis of Amine 78

Amine 78 was synthesized (in a 90% yield) in the same manner as in Synthesis Example 55, except that 2-(2-aminoethoxy)ethanol was used in place of 2-aminoethanol.

Synthesis Example 79

Synthesis of Amine 79

Amine 79 was synthesized (in a 74% yield) in the same manner as in Synthesis Example 68, except that 2-(2-aminoethoxy)ethanol was used in place of 2-aminoethanol.

Synthesis Example 80

Synthesis of Amine 80

A mixture composed of 21.9 g of amine 34, 10.4 g of (1,3-dioxolan-4-yl)methanol, 100 mg of sodium methoxide, and 60 g of benzene was heated under reflux for 5 hours, during which time the methanol resulting from the reaction was distilled off. The reaction mixture was concentrated under reduced pressure and then purified by vacuum distillation to obtain amine 80 (in a 90% yield).

Synthesis Example 81

Synthesis of Amine 81

Amine 81 was synthesized (in a 81% yield) in the same manner as in Synthesis Example 80, except that tetrahydropyran-4-ol was used in place of (1,3-dioxolan-4-yl)methanol.

REFERENCE EXAMPLES AND COMPARATIVE REFERENCE EXAMPLES

Ester group-containing tertiary amine compounds in accordance with the present invention were added to photoresists, and the effect of their addition was evaluated according to the method described below. With respect to the polymers used, their structure, weight-average molecular weight (Mw), and ratio of Mw to number-average molecular weight (Mn) will be given later. Average molecular weights were determined on a polystyrene basis by gel permeation chromatography (GPC).

A resist solution was prepared by dissolving a polymer, an acid generator, a base, a dissolution inhibitor and a crosslinker in a solvent mixture composed of propylene glycol monomethyl ether acetate (PGMEA) and ethyl lactate (EL) in a weight ratio of 70:30, and filtering this solution through a Teflon filter having a pore diameter of 0.1 μm.

Then, a substrate was prepared by forming a 55 nm thick film of DUV-30 (manufactured by Nissan Chemical Industries Ltd.) on a silicon wafer so that its reflectivity to KrF light (248 nm) was reduced to 1% or less. The above resist solution was spin-coated onto the substrate and baked on a hot plate at 100° C. for 90 seconds to form a resist film having a thickness of 550 nm.

Using an excimer laser stepper (NSR-S202A, manufactured by Nikon Corp.; NA=0.5; σ=0.75; 2/3 annular illumination), the resist film was exposed to light with variation in exposure and with a shift of the focus. Immediately after exposure, the resist film was baked at 110° C. for 90 seconds and developed by soaking it in a 2.38% aqueous solution of tetramethylammonium hydroxide for 60 seconds.

The resist patterns thus obtained were evaluated in the following manner. The results are shown in the reference example tables (Tables 1 and 2) and the comparative reference example table (Table 3).

(Evaluation Method)

The exposure which can resolve 0.16 μm lines and spaces 1:1 was defined as the optimum exposure (Eop) and used for the evaluation of the resist sensitivity. Then, the focus margin was determined at this exposure. The focus margin was defined on the basis of the fact that the patterns showed no film loss and the pattern size was 0.16 μm±10% or less.

It has been confirmed by the results thus obtained that the photoresists prepared by adding the ester group-containing tertiary amine compounds of the present invention have a much wider focus margin, as compared with conventional photoresists.

TABLE 1

| Reference Example | Polymer (parts by weight) | Acid generator (parts by weight) | Base (parts by weight) | Dissolution inhibitor or crosslinker (parts by weight) | Sensitivity (mJ/cm$^2$) | Focus margin (μm) |
|---|---|---|---|---|---|---|
| 1 | 1 (100) | PAG2 (2) | Amine2 (0.1) | — | 30 | 0.9 |
| 2 | 1 (100) | PAG2 (2) | Amine10 (0.1) | — | 35 | 0.8 |
| 3 | 1 (100) | PAG2 (2) | Amine17 (0.1) | — | 31 | 1.0 |
| 4 | 1 (100) | PAG2 (2) | Amine18 (0.12) | — | 30 | 1.0 |
| 5 | 1 (100) | PAG2 (2) | Amine19 (0.12) | — | 33 | 1.0 |
| 6 | 1 (100) | PAG2 (2) | Amine35 (0.12) | — | 28 | 1.0 |
| 7 | 1 (100) | PAG2 (2) | Amine39 (0.1) | — | 32 | 1.0 |
| 8 | 1 (100) | PAG2 (2) | Amine57 (0.12) | — | 39 | 1.0 |
| 9 | 1 (100) | PAG2 (2) | Amine81 (0.16) | — | 38 | 1.0 |
| 10 | 1 (100) | PAG2 (2) | Amine73 (0.16) | — | 40 | 1.0 |
| 11 | 2 (100) | PAG2 (2) | Amine73 (0.1) | — | 35 | 0.6 |
| 12 | 3 (100) | PAG2 (2) | Amine73 (0.1) | — | 31 | 1.1 |
| 13 | 4 (100) | PAG2 (2) | Amine73 (0.1) | crosslinker (15) | 38 | 0.8 |
| 14 | 5 (100) | PAG1 (2) | Amine73 (0.1) | — | 33 | 0.8 |
| 15 | 6 (100) | PAG1 (2) | Amine73 (0.1) | — | 46 | 1.0 |
| 16 | 7 (100) | PAG1 (2) | Amine73 (0.1) | — | 48 | 1.0 |
| 17 | 8 (100) | PAG1 (2) | Amine73 (0.1) | — | 42 | 1.0 |
| 18 | 9 (100) | PAG1 (2) | Amine73 (0.1) | — | 43 | 0.9 |

TABLE 2

| Reference Example | Polymer (parts by weight) | Acid generator (parts by weeight) | Base (parts by weight) | Dissolution inhibitor or crosslinker (parts by weight) | Sensitivity (mJ/cm$^2$) | Focus margin (μm) |
|---|---|---|---|---|---|---|
| 19 | 10 (100) | PAG1 (2) | Amine73 (0.1) | — | 40 | 1.1 |
| 20 | 11 (100) | PAG1 (2) | Amine73 (0.1) | — | 41 | 0.8 |
| 21 | 12 (100) | PAG1 (2) | Amine73 (0.1) | — | 39 | 0.9 |
| 22 | 13 (100) | PAG1 (2) | Amine73 (0.1) | — | 44 | 0.9 |
| 23 | 14 (100) | PAG1 (2) | Amine73 (0.1) | — | 43 | 0.8 |
| 24 | 2 (100) | PAG2 (2) | Amine73 (0.1) | DRI (20) | 31 | 0.8 |

TABLE 3

| Compartative Reference Example | Polymer (parts by weight) | Acid generator (parts by weight) | Base (parts by weight) | Dissolution inhibitor or crosslinker (parts by weight) | Sensitivity (mJ/cm$^2$) | Focus margin (μm) |
|---|---|---|---|---|---|---|
| 1 | 1 (100) | PAG2 (2) | — | — | 5 | 0 |

TABLE 3-continued

| Compartative Reference Example | Polymer (parts by weight) | Acid generator (parts by weight) | Base (parts by weight) | Dissolution inhibitor or crosslinker (parts by weight) | Sensitivity (mJ/cm$^2$) | Focus margin (μm) |
|---|---|---|---|---|---|---|
| 2 | 1 (100) | PAG2 (2) | Proton sponge (0.2) | — | 30 | 0.4 |
| 3 | 1 (100) | PAG2 (2) | DBN (0.1) | — | 25 | 0.4 |
| 4 | 1 (100) | PAG2 (2) | trietanol-amine (0.1) | — | 28 | 0.6 |
| 5 | 2 (100) | PAG2 (2) | DBN (0.1) | — | 35 | 0.2 |
| 6 | 3 (100) | PAG2 (2) | DBN (0.1) | — | 31 | 0.5 |
| 7 | 4 (100) | PAG2 (2) | DBN (0.1) | crosslinker (15) | 38 | 0.3 |
| 8 | 5 (100) | PAG1 (2) | DBN (0.1) | — | 33 | 0.3 |
| 9 | 6 (100) | PAG1 (2) | DBN (0.1) | — | 46 | 0.6 |
| 10 | 7 (100) | PAG1 (2) | DBN (0.1) | — | 48 | 0.6 |
| 11 | 8 (100) | PAG1 (2) | DBN (0.1) | — | 42 | 0.3 |
| 12 | 9 (100) | PAG1 (2) | DBN (0.1) | — | 35 | 0.4 |
| 13 | 10 (100) | PAG1 (2) | DBN (0.1) | — | 37 | 0.3 |
| 14 | 11 (100) | PAG1 (2) | DBN (0.1) | — | 40 | 0.5 |
| 15 | 12 (100) | PAG1 (2) | DBN (0.1) | — | 39 | 0.4 |
| 16 | 13 (100) | PAG1 (2) | DBN (0.1) | — | 36 | 0.3 |
| 17 | 14 (100) | PAG1 (2) | DBN (0.1) | — | 37 | 0.3 |
| 18 | 2 (100) | PAG2 (2) | DBN (0.1) | DRI (20) | 31 | 0.4 |

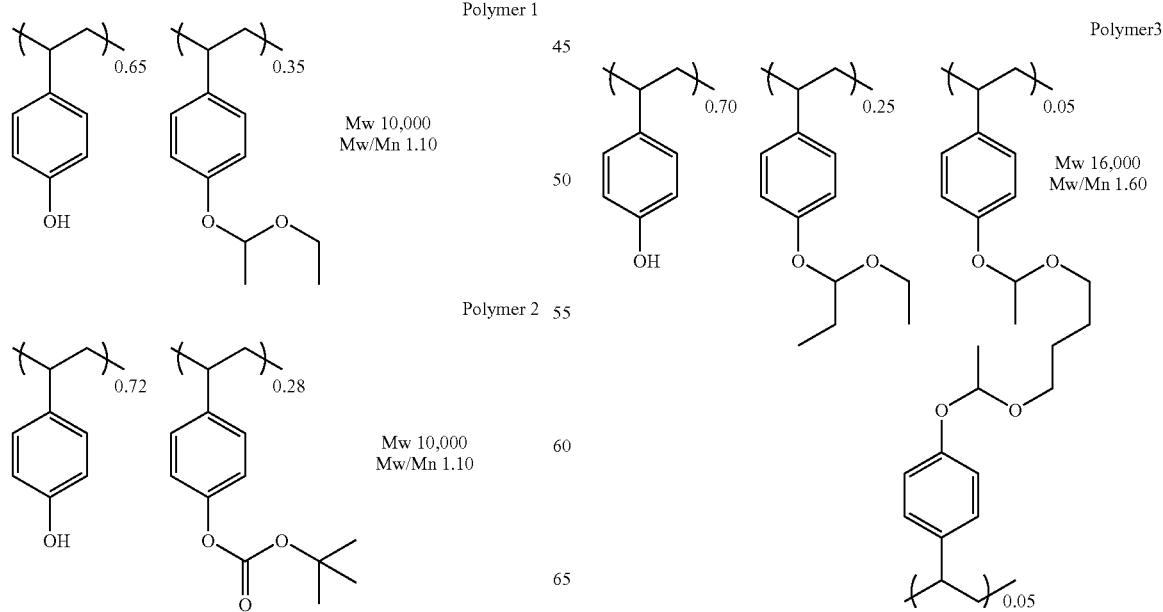

-continued
Polymer 4
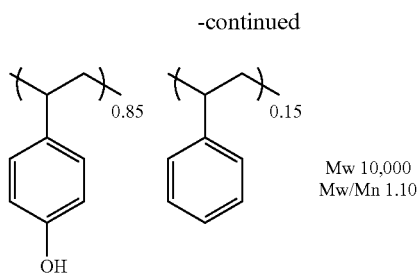
Mw 10,000
Mw/Mn 1.10
Polymer 5
Mw 12,000
Mw/Mn 1.60
Polymer 6
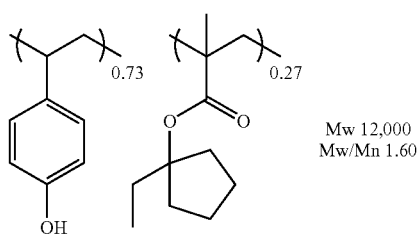
Mw 10,000
Mw/Mn 1.60
Polymer 7
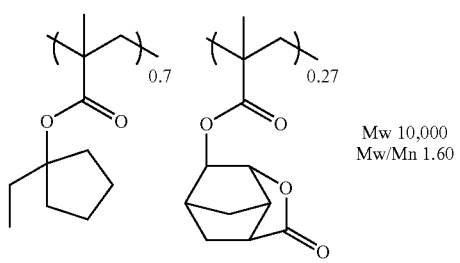
Mw 13,000
Mw/Mn 1.85
Polymer 8
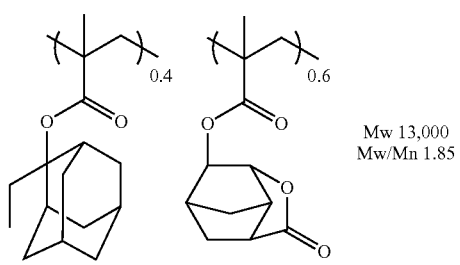
Mw 10,000
Mw/Mn 1.50
-continued
Polymer 9
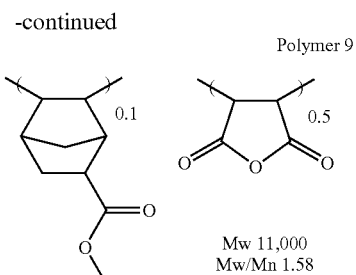
Mw 11,000
Mw/Mn 1.58
Polymer 10
Mw 18,000
Mw/Mn 2.0
Polymer 11
Mw 10,000
Mw/Mn 1.50
Polymer 12
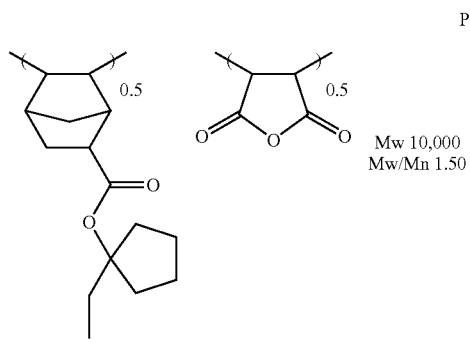
Mw 10,400
Mw/Mn 1.67

-continued

Polymer 13

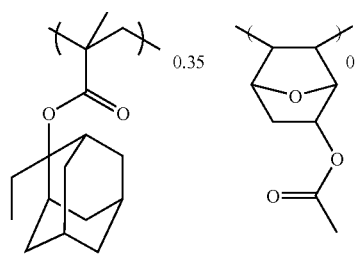
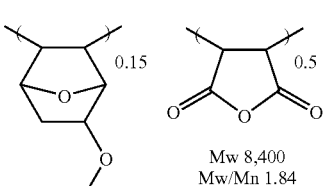

Mw 8,400
Mw/Mn 1.84

Polymer 14

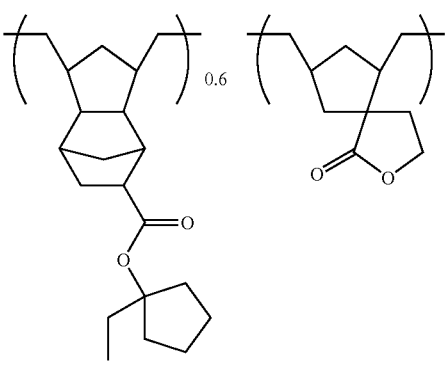

Mw 13,000
Mw/Mn 1.20

PAG 1

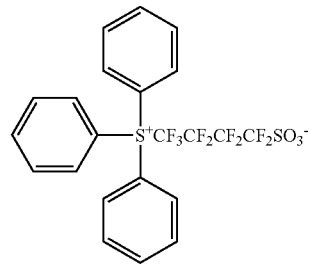

PAG 2

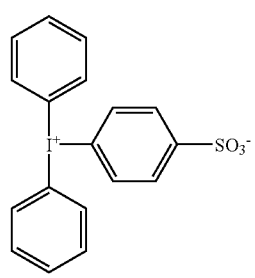

DRI 1

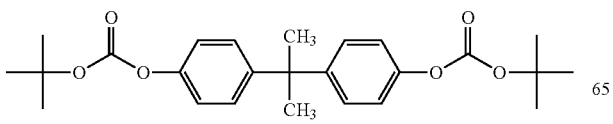

-continued

Crosslinker 1

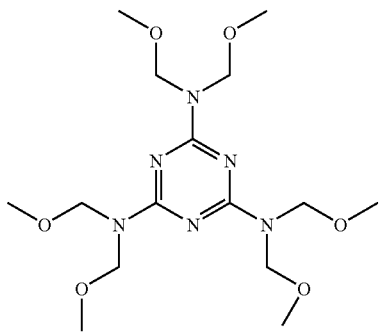

The invention claimed is:

1. An ester group-containing tertiary amine compound represented by the following general formula (1)

$$(R^1OCH_2CH_2)_nN(CH_2CH_2CO_2R^2)_{3-n} \qquad (1)$$

wherein n is 1 or 2; and $R^1$ independently represents a straight-chain, branched or cyclic saturated alkyl group of 1 to 20 carbon atoms which may contain an ether, or carbonyloxy group; and $R^2$ independently represents a straight-chain, branched or cyclic saturated alkyl group of 1 to 20 carbon atoms which may contain an ether, carbonyl or carbonyloxy group.

2. An ester group-containing tertiary amine compound as claimed in claim 1 wherein, in the above general formula (1), $R^1$ has 1 to 10 carbon atoms and $R^2$ has 2 to 10 carbon atoms.

3. An ester group-containing tertiary amine compound as claimed in claim 1 wherein, in the above general formula (1), $R^2$ has 2 to 10 carbon atoms.

4. An ester group-containing tertiary amine compound as claimed in claim 1 wherein, in the above general formula (1), $R^1$ is a methyl group and $R^2$ has 2 to 10 carbon atoms.

5. An ester group-containing tertiary amine compound as claimed in claim 2 wherein, in the above general formula (1), $R^1$ is a methyl group and $R^2$ has 2 to 10 carbon atoms.

6. An ester group-containing tertiary amine compound represented by the following general formula (1)

$$(R^1OCH_2CH_2)_nN(CH_2CH_2CO_2R^2)_{3-n} \qquad (1)$$

wherein n is 1; and $R^1$ and $R^2$ each independently represents a straight-chain, branched or cyclic saturated alkyl group of 1 to 20 carbon atoms which may contain an ether, carbonyl or carbonyloxy group; and selected from the group consisting of:

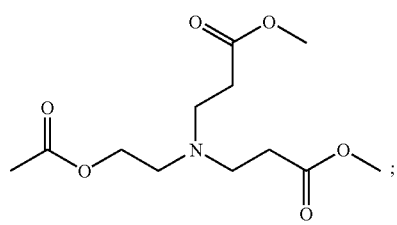

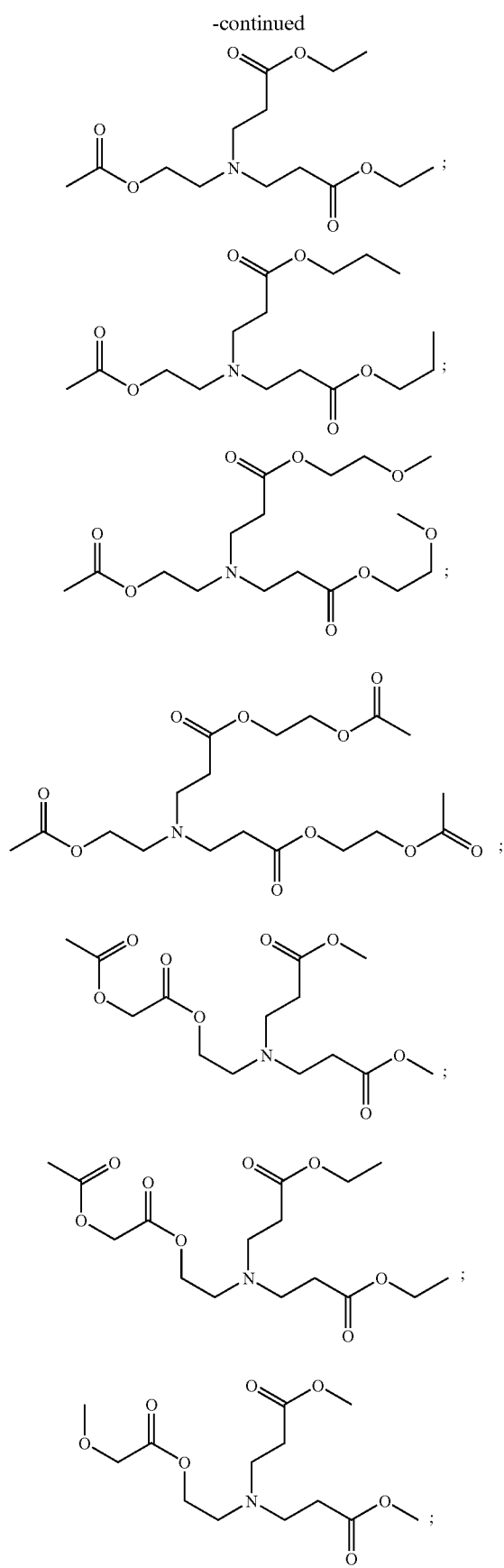
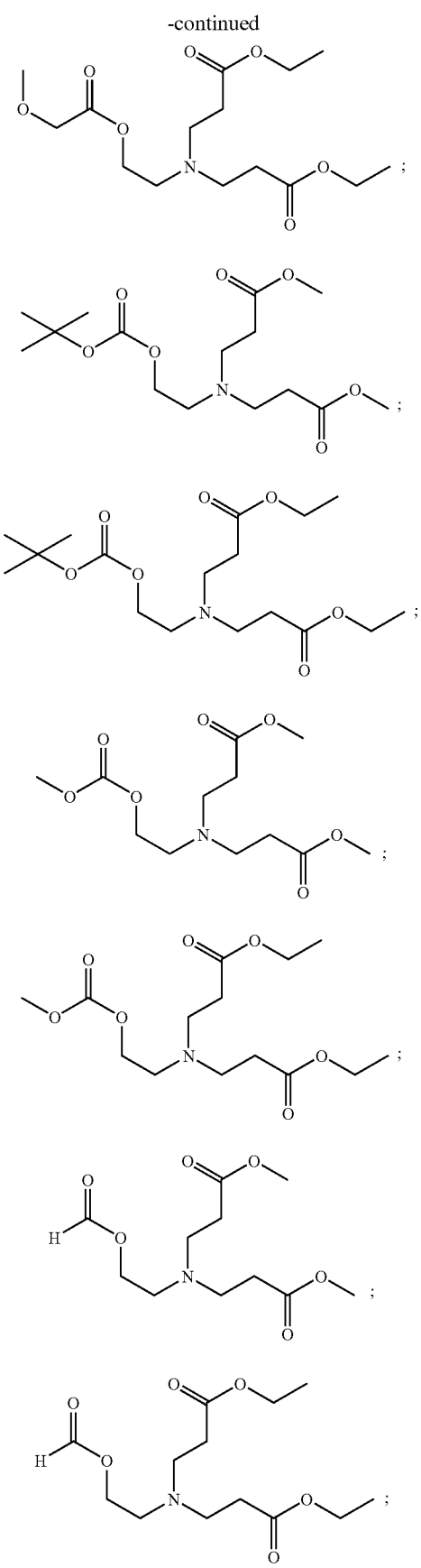

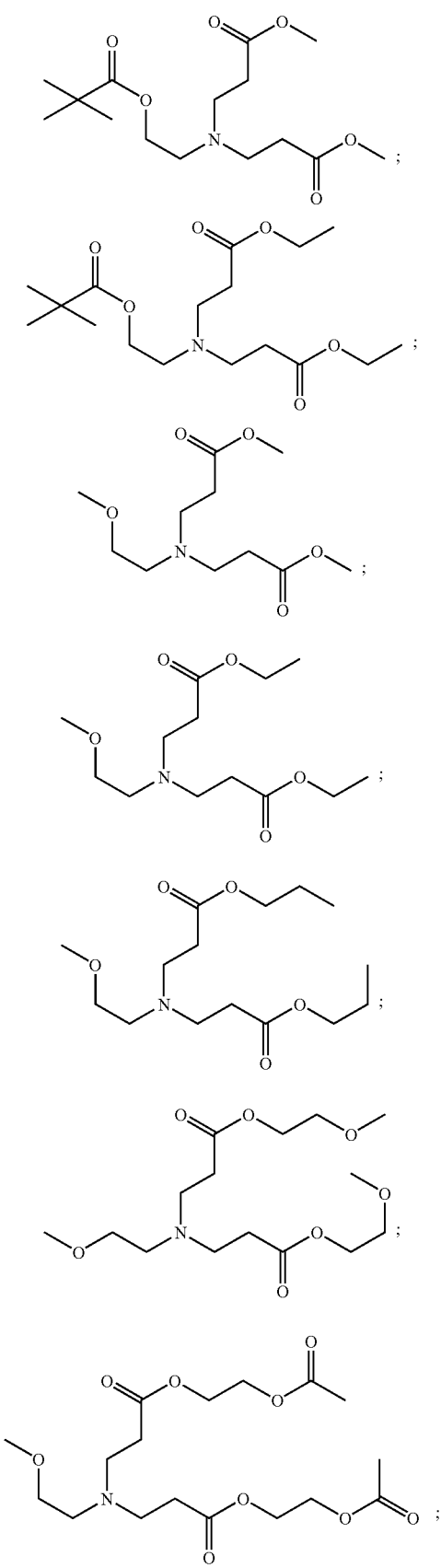

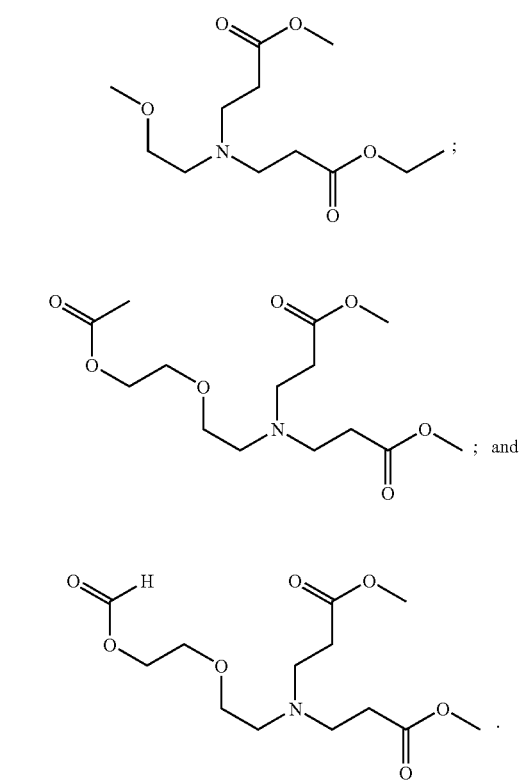

7. An ester group-containing tertiary amine compound represented by the following general formula (1)

$$(R^1OCH_2CH_2)_nN(CH_2CH_2CO_2R^2)_{3-n} \qquad (1)$$

wherein n is 2; and $R^1$ and $R^2$ each independently represents a straight-chain, branched or cyclic saturated alkyl group of 1 to 20 carbon atoms which may contain an ether, carbonyl or carbonyloxy group; and selected from the group consisting of:

Amine 80

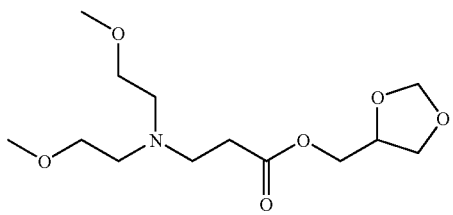

Amine 81

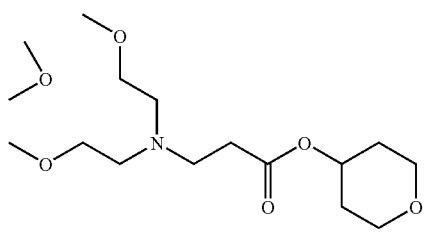

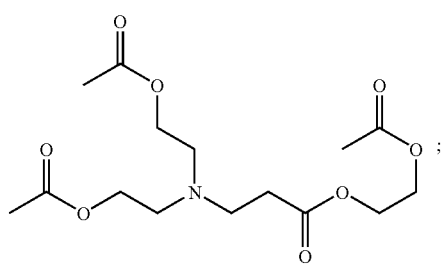
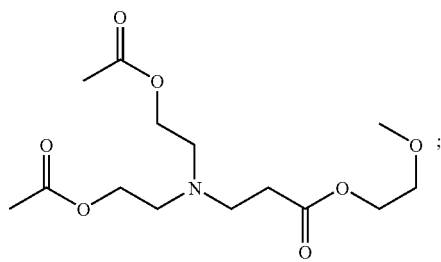
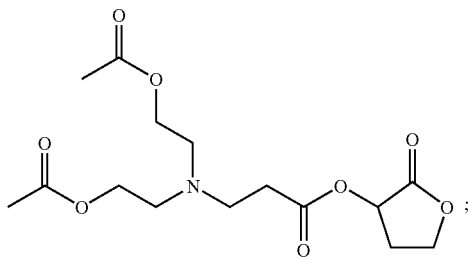
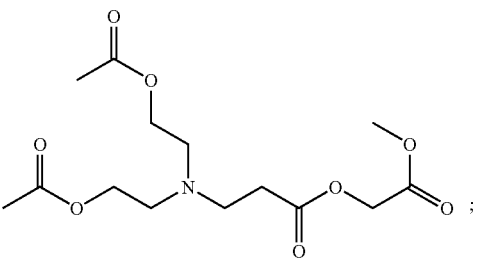
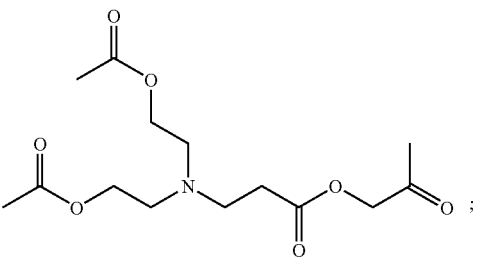
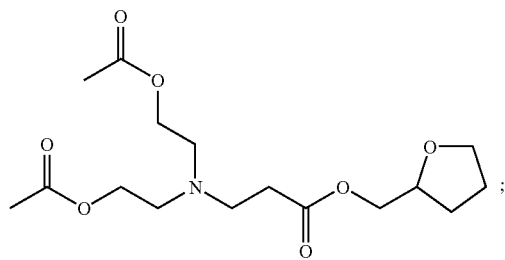
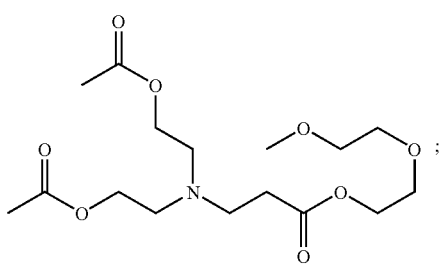
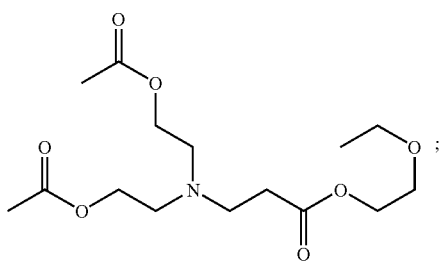
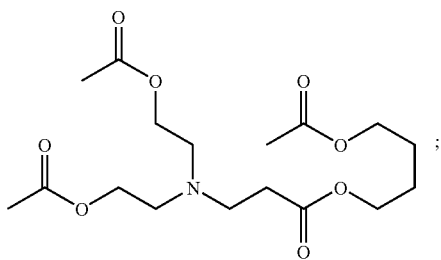
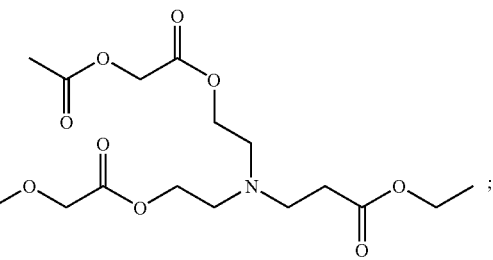
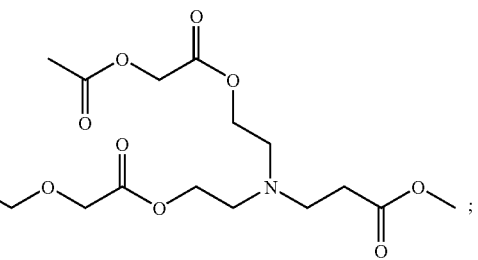

-continued
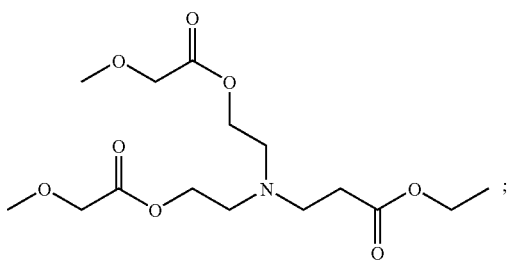
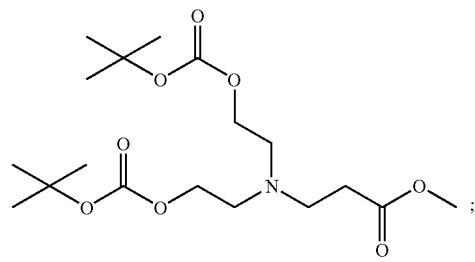
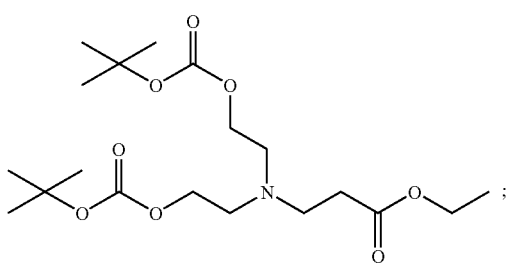
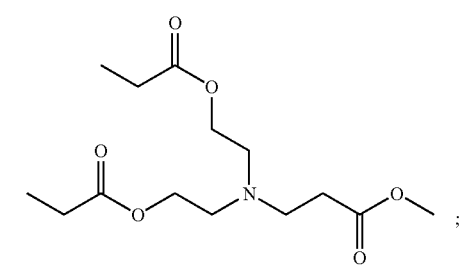
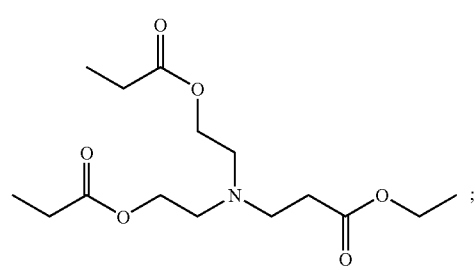
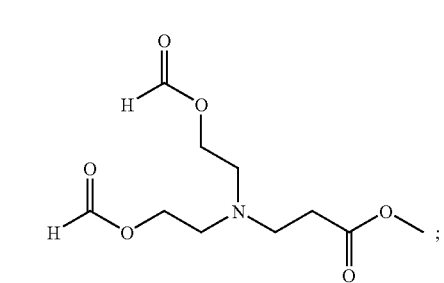
-continued
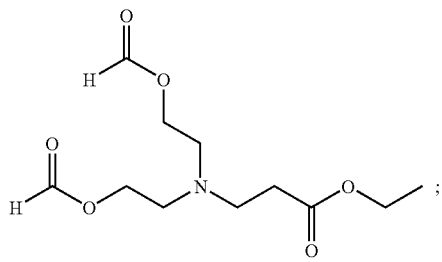
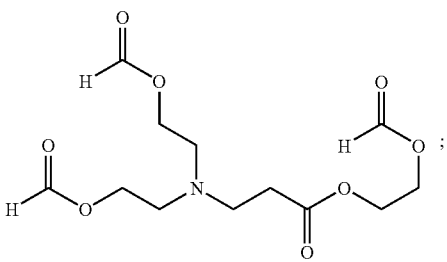
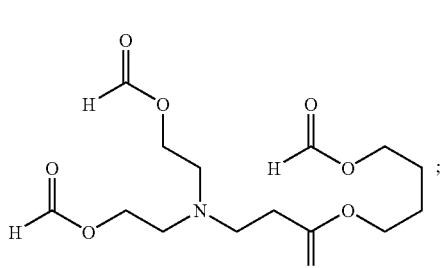
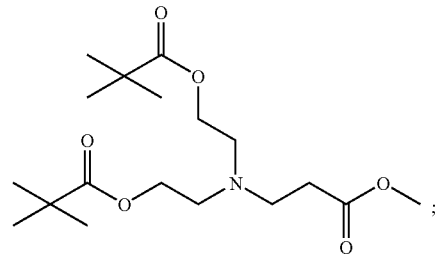
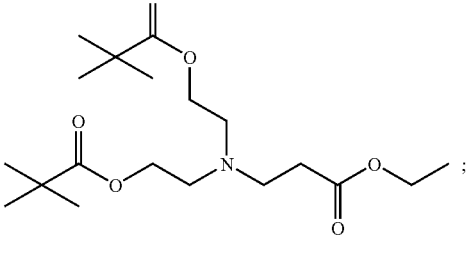
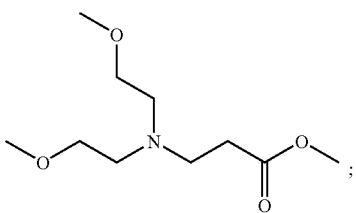

-continued
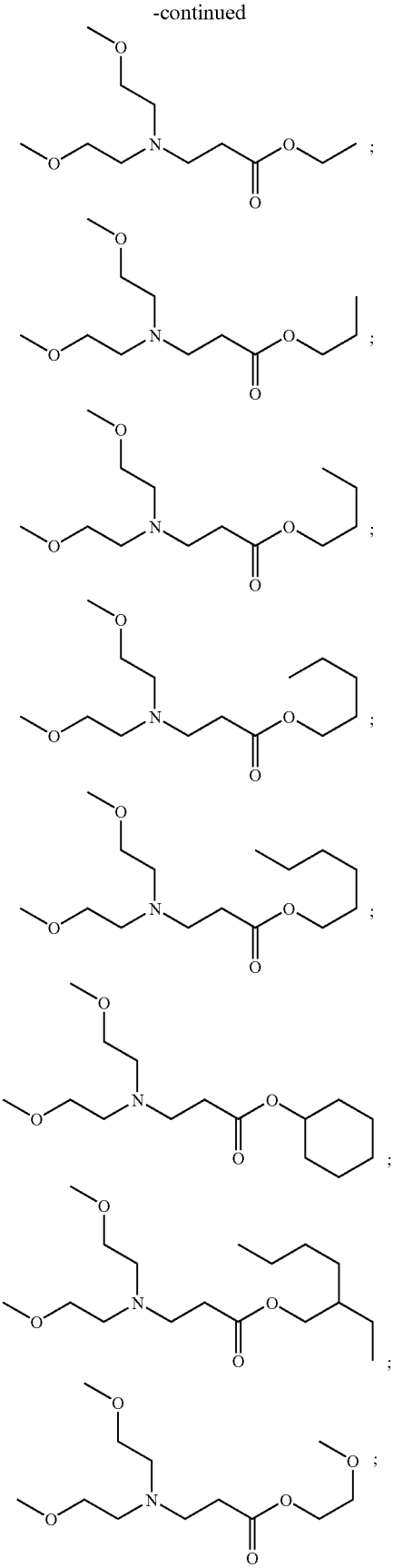
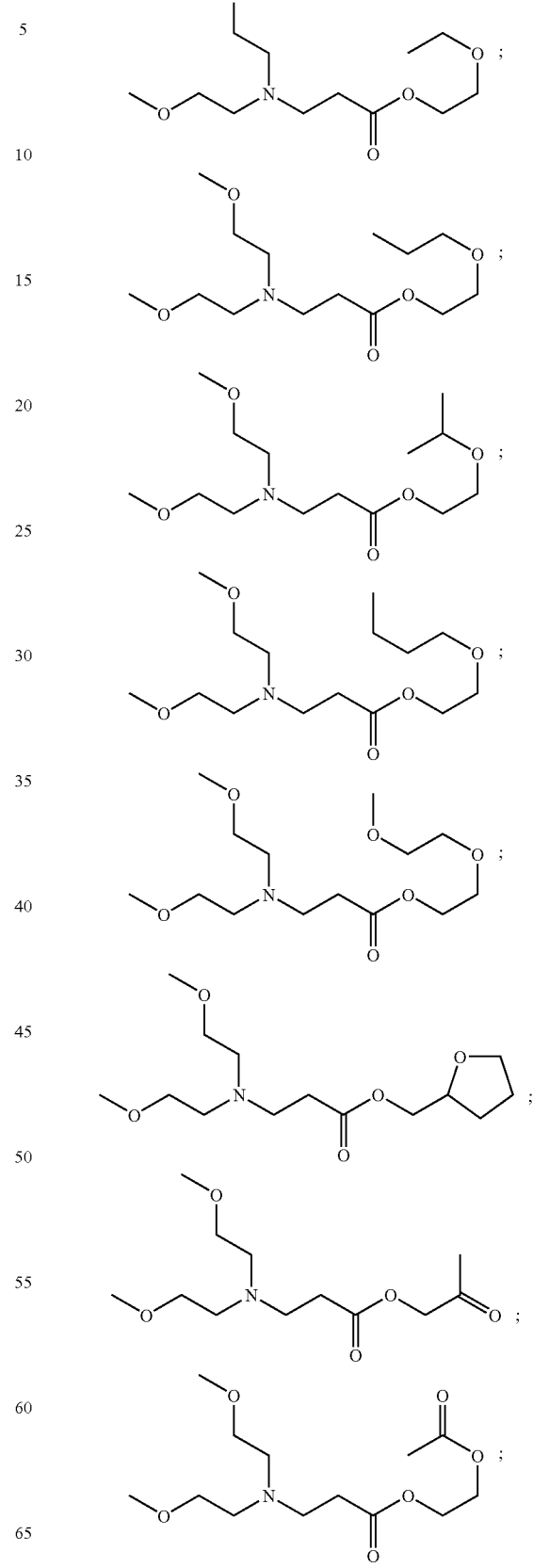

-continued
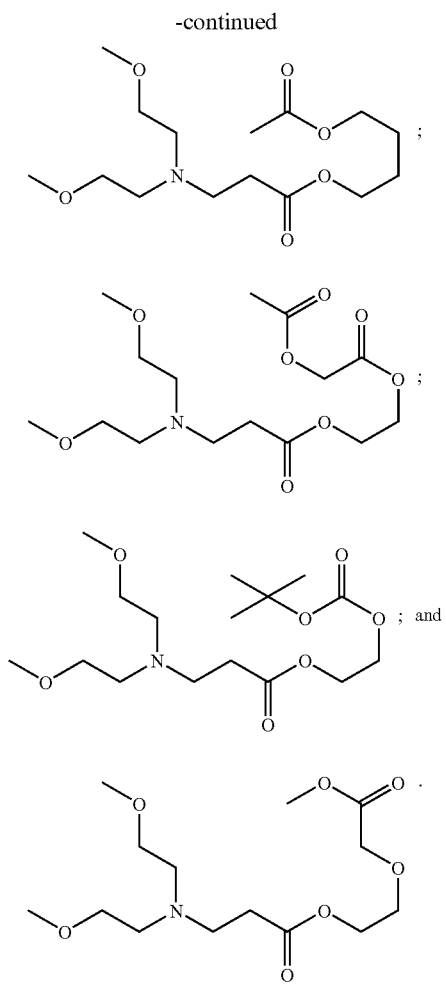
8. An ester group-containing tertiary amine compound selected from the group consisting of:
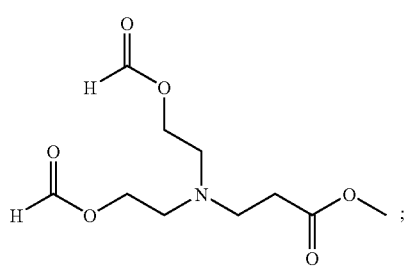
-continued
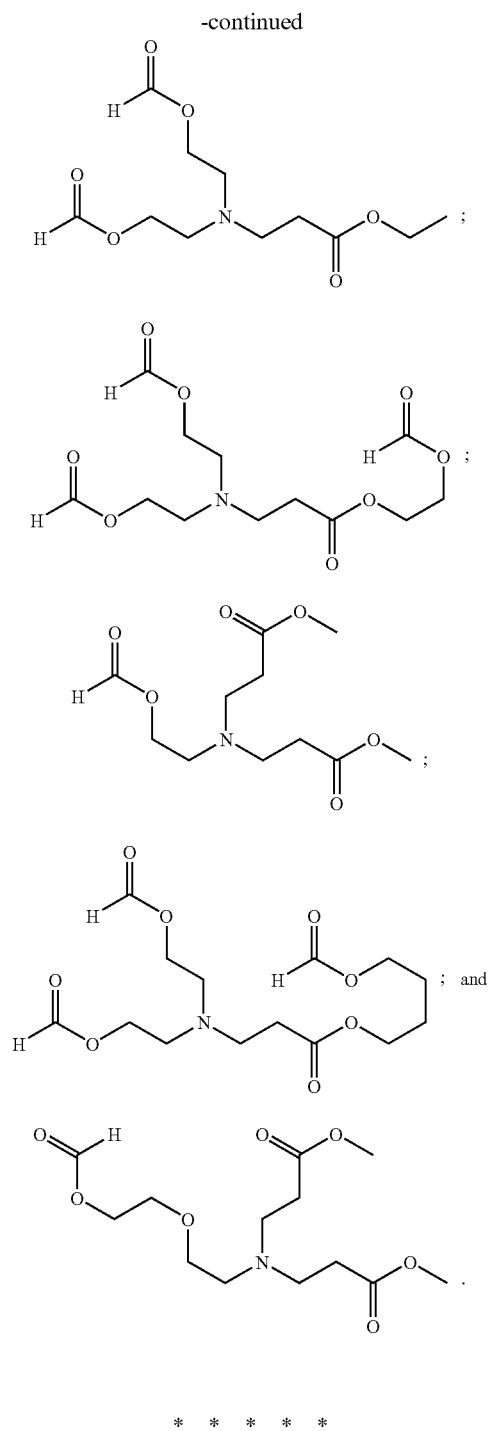
* * * * *